`US011155857B2`

United States Patent
Li et al.

(10) Patent No.: US 11,155,857 B2
(45) Date of Patent: Oct. 26, 2021

(54) METHODS FOR MEASURING RNA TRANSLATION RATES

(71) Applicant: Dana-Farber Cancer Institute, Inc., Boston, MA (US)

(72) Inventors: Ben B. Li, Boston, MA (US); Jean Zhao, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 300 days.

(21) Appl. No.: 16/309,551

(22) PCT Filed: Jun. 23, 2017

(86) PCT No.: PCT/US2017/039001
§ 371 (c)(1),
(2) Date: Dec. 13, 2018

(87) PCT Pub. No.: WO2018/005283
PCT Pub. Date: Jan. 4, 2018

(65) Prior Publication Data
US 2019/0177782 A1    Jun. 13, 2019

Related U.S. Application Data
(60) Provisional application No. 62/355,122, filed on Jun. 27, 2016.

(51) Int. Cl.
| C12Q 1/6851 | (2018.01) |
| C12Q 1/6806 | (2018.01) |
| C12Q 1/6853 | (2018.01) |
| C12Q 1/686  | (2018.01) |
| C12Q 1/6876 | (2018.01) |

(52) U.S. Cl.
CPC ........ *C12Q 1/6851* (2013.01); *C12Q 1/6806* (2013.01); *C12Q 1/686* (2013.01); *C12Q 1/6853* (2013.01); *C12Q 1/6876* (2013.01); *C12Q 2521/107* (2013.01); *C12Q 2521/327* (2013.01); *C12Q 2527/127* (2013.01); *C12Q 2561/113* (2013.01); *C12Y 207/07049* (2013.01)

(58) Field of Classification Search
CPC .............. C12N 15/1041; C12Q 1/6886; C12Q 1/6874; C12Q 1/68
See application file for complete search history.

(56) References Cited

U.S. PATENT DOCUMENTS 7,572,577 B2    8/2009  He et al.
2002/0177701 A1*  11/2002  Weissman ............ C12Q 1/6855
                                                         536/24.3
(Continued)

OTHER PUBLICATIONS

Ingolia et al. The ribosome profiling strategy for monitoring translation in vivo by deep sequencing of ribosome-protected mRNA fragments, 2013, Nat Protoc. ; 7(8): pp. 1534-1550. (Year: 2013).*
(Continued)

*Primary Examiner* — Jehanne S Sitton
*Assistant Examiner* — Daniel W Nielsen
(74) *Attorney, Agent, or Firm* — Foley Hoag LLP

(57) ABSTRACT

The present invention provides methods for measuring translation rates of RNA associated with a ribosome (e.g., mRNA) in a rapid, cost-effective, and targeted manner.

17 Claims, 9 Drawing Sheets
Specification includes a Sequence Listing.

(56) References Cited

U.S. PATENT DOCUMENTS

2004/0023256 A1 2/2004 Puglisi et al.
2010/0120625 A1 5/2010 Weissman et al.

OTHER PUBLICATIONS

Ghandi et al., Omacetaxine: a protein translation inhibitor for treatment of chronic myelogenous leukemia, Clin Cancer Res. Apr. 1, 2014; 20(7): pp. 1735-1740 (Year: 2014).*
Park et al., Versatile Synthetic Route to Cycloheximide and Analogues That Potently Inhibit Translation Elongation, Angewandte Chemie International Edition. Feb. 29, 2019; 58(16): pp. 5387-5391 (Year: 2019).*
Nakae et al., Migrastatin, a new inhibitor of tumor cell migration from *Streptomyces* sp. MK929-43F1. Taxonomy, fermentation, isolation and biological activities, Journal of Antibiotics (Tokyo).; 53(10):1130-6, Oct. 1, 2000; 20(7): pp. 1130-1136 (Year: 2000).*
Extended European Search Report for EP Application No. EP 17820976 dated Feb. 17, 2020.
Gao et al., "Quantitative profiling of initiating ribosomes in vivo," Nature Methods, 12(2):147-153 (2015).
Ingolia et al., "Ribosome Profiling of Mouse Embryonic Stem Cells Reveals the Complexity and Dynamics of Mammalian Proteomes," Cell, 147(4):789-802 (2011).
Ingolia et al., "The ribosome profiling strategy for monitoring translation in vivo by deep sequencing of ribosome-protected mRNA fragments," Nature Protocols, 7(8):1534-1550 (2012).
Lee et al., "Global mapping of translation initiation sites in mammalian cells at single-nucleotide resolution," PNAS, 109(37):E2424-E2432 (2012).
International Search Report and Written Opinion for International Application No. PCT/US17/39001 dated Sep. 27, 2017.
Miettinen et al., "Modified ribosome profiling reveals high abundance of ribosome protected mRNA fragments derived from 3' untranslated regions," Nucleic Acids Res, 43(2): 1019-1034 (2014).

* cited by examiner

Figure 2 (cont.)

Primer A

5' AGCGGATAACAATTTCACACAGGAAACAGCTATGAC........
                                      |_____|
                                       M13 reverse
                                   |_____|
                                       primer BR Sequence derived from pUC19 plasmid by the Messing lab previously described in Norrander et al. (1983) Gene 26:101-106

| Gene | Fold change in translation rate, gene vs. ACTB, Torin-1 (100 nM, 1 h) vs. DMSO | | | | | | | |
|---|---|---|---|---|---|---|---|---|
| | MDA-MB-468 | | | | HMEC-CT2 | | | |
| | invention subject | | ribozome profiling | | invention subject | | replicate 2 | |
| | replicate 1 | replicate 2 | replicate 1 | replicate 2 | replicate 1 | replicate 2 | | |
| RPS1A | 0.16 | 0.23 | 0.27 | 0.27 | 0.26 | 0.23 | | |
| RPS25 | 0.36 | 0.45 | 0.39 | 0.29 | 0.41 | 0.37 | | |
| RPS-7 | 0.32 | 0.54 | 0.32 | 0.17 | 0.43 | 0.37 | | |
| RPL7A | 0.40 | 0.49 | 0.26 | 0.28 | 0.41 | 0.30 | | |
| RPL31 | 0.24 | 0.21 | 0.20 | 0.17 | 0.25 | 0.20 | | |
| EEF1A1 | 0.13 | 0.13 | 0.15 | 0.13 | 0.12 | 0.10 | | |
| GAPDH | 0.35 | 0.51 | 0.43 | 0.39 | 0.33 | 0.28 | | |
| R9PA0 | 0.35 | 0.39 | 0.39 | 0.46 | 0.58 | 0.55 | | |
| YBT1 | 0.29 | 0.28 | 0.32 | 0.56 | 0.53 | 0.19 | | |
| ATP5F1 | 0.35 | 1.08 | 0.96 | 0.94 | 1.23 | 0.76 | | |
| HSP3A | 1.39 | 1.49 | 1.19 | 1.17 | 1.49 | 1.37 | | |
| KRT8 | 0.72 | 1.08 | 0.75 | 1.02 | 1.01 | 0.99 | | |
| NDUFC2 | 1.46 | 1.65 | 1.09 | 1.19 | 1.36 | 1.02 | | |
| FBTA | 1.07 | 1.20 | 1.06 | 1.11 | 1.47 | 1.59 | | |
| TUBA1B | 1.13 | 1.26 | 1.02 | 1.14 | 0.97 | 0.91 | | |
| VAEA | 1.04 | 1.35 | 1.05 | 1.19 | 1.32 | 1.58 | | |
| YWHAQ | 1.33 | 1.39 | 1.12 | 1.19 | 1.33 | 1.32 | | |

SEQUENCE LISTING

<160> NUMBER OF SEQ ID NOS: 51

<210> SEQ ID NO 1
<211> LENGTH: 56
<212> TYPE: DNA
<213> ORGANISM: Artificial Sequence
<220> FEATURE:

-continued

```
<223> OTHER INFORMATION: /note="Description of Artificial Sequence:
      Synthetic primer"

<400> SEQUENCE: 1
agcggataac aatttcacac aggcaggaaa cagctatgac agtcttttcc tttccc            56

<210> SEQ ID NO 2
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 2
cccctaaaag ccaaaatggg                                                    20

<210> SEQ ID NO 3
<211> LENGTH: 49
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 3
agcggataac aatttcacac aggcaggaaa cagctatgac gggcggcgg                    49

<210> SEQ ID NO 4
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 4
gatcctggtg tcgccat                                                       17

<210> SEQ ID NO 5
<211> LENGTH: 53
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 5
agcggataac aatttcacac aggcaggaaa cagctatgac tttgctgagg ccg               53

<210> SEQ ID NO 6
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 6
tttccctctc ccaacatgg                                                     19

<210> SEQ ID NO 7
<211> LENGTH: 53
<212> TYPE: DNA
<213> ORGANISM: Artificial Sequence
```

```
<220> FEATURE:
<223> OTHER INFORMATION: /note="Description of Artificial Sequence:
      Synthetic primer"

<400> SEQUENCE: 7
agcggataac aatttcacac aggcaggaaa cagctatgac cggttcgaca gtc          53

<210> SEQ ID NO 8
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 8
tcagatcgat ctaagatggc ga                                            22

<210> SEQ ID NO 9
<211> LENGTH: 55
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 9
agcggataac aatttcacac aggcaggaaa cagctatgac ggcgatatca tcatc        55

<210> SEQ ID NO 10
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 10
cgccagctca ccatgga                                                  17

<210> SEQ ID NO 11
<211> LENGTH: 55
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 11
agcggataac aatttcacac aggcaggaaa cagctatgac cttcacgaag atctg        55

<210> SEQ ID NO 12
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 12
gatcgtcact tgacaatgca g                                             21

<210> SEQ ID NO 13
<211> LENGTH: 23
<212> TYPE: DNA
<213> ORGANISM: Artificial Sequence
<220> FEATURE:
```

```
<223> OTHER INFORMATION: /note="Description of Artificial Sequence:
      Synthetic primer"

<400> SEQUENCE: 13
agcggataac aatttcacac agg                                              23

<210> SEQ ID NO 14
<211> LENGTH: 50
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 14
agcggataac aatttcacac aggaaacagc tatgacgttc ttgccaaccg                 50

<210> SEQ ID NO 15
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 15
tctctgacca gcaccatgg                                                   19

<210> SEQ ID NO 16
<211> LENGTH: 49
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 16
agcggataac aatttcacac aggaaacagc tatgactcgt ccttaggcg                  49

<210> SEQ ID NO 17
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 17
tctccgagct tcgcaatgc                                                   19

<210> SEQ ID NO 18
<211> LENGTH: 51
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 18
agcggataac aatttcacac aggaaacagc tatgacatcc tttgcgagag g               51

<210> SEQ ID NO 19
<211> LENGTH: 20
<212> TYPE: DNA
<213> ORGANISM: Artificial Sequence
<220> FEATURE:
<223> OTHER INFORMATION: /note="Description of Artificial Sequence:
```

Synthetic primer"

<400> SEQUENCE: 19
tacgcacacg agaacatgcc                                                    20

<210> SEQ ID NO 20
<211> LENGTH: 52
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 20
agcggataac aatttcacac aggaaacagc tatgaccttc tttcctttcg gc                 52

<210> SEQ ID NO 21
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 21
cccgccgccc aagat                                                         15

<210> SEQ ID NO 22
<211> LENGTH: 50
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 22
agcggataac aatttcacac aggaaacagc tatgactccc tttgtgttcg                   50

<210> SEQ ID NO 23
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 23
cagtaattcg ccaaaatgac gaa                                                23

<210> SEQ ID NO 24
<211> LENGTH: 52
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 24
agcggataac aatttcacac aggaaacagc tatgacagtc ttttcctttc cc                 52

<210> SEQ ID NO 25
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 25
cccctaaaag ccaaaatggg                                                    20

<210> SEQ ID NO 26
<211> LENGTH: 50
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 26
agcggataac aatttcacac aggaaacagc tatgacgacc ttcaccttcc                   50

<210> SEQ ID NO 27
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 27
catcgctcag acaccatgg                                                     19

<210> SEQ ID NO 28
<211> LENGTH: 49
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 28
agcggataac aatttcacac aggaaacagc tatgacaggt cccttggac                    49

<210> SEQ ID NO 29
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 29
tacaccccag caaccatgt                                                     19

<210> SEQ ID NO 30
<211> LENGTH: 52
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 30
agcggataac aatttcacac aggaaacagc tatgacgtcc cggtagataa tc                52

<210> SEQ ID NO 31
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31
ccttcagtcg ccatcatgat						20

<210> SEQ ID NO 32
<211> LENGTH: 48
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32
agcggataac aatttcacac aggaaacagc tatgacccac ccgggaca			48

<210> SEQ ID NO 33
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
ggactttcgt tgaccatgct g						21

<210> SEQ ID NO 34
<211> LENGTH: 51
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 34
agcggataac aatttcacac aggaaacagc tatgacctgc tttgtacgag c		51

<210> SEQ ID NO 35
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 35
ggaggtctct gtaccatggc						20

<210> SEQ ID NO 36
<211> LENGTH: 50
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
agcggataac aatttcacac aggaaacagc tatgacactt gactggcgag		50

<210> SEQ ID NO 37
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
caggaacaag ccaccatgt                                              19

<210> SEQ ID NO 38
<211> LENGTH: 47
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
agcggataac aatttcacac aggaaacagc tatgaccgcc gtgcgat            47

<210> SEQ ID NO 39
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 39
ggaaacggcg tcaccat                                                17

<210> SEQ ID NO 40
<211> LENGTH: 48
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 40
agcggataac aatttcacac aggaaacagc tatgaccggt ggggttga          48

<210> SEQ ID NO 41
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 41
cgtgtactat tagccatggt ca                                          22

<210> SEQ ID NO 42
<211> LENGTH: 50
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42
agcggataac aatttcacac aggaaacagc tatgacgaga tgcactcacg        50

<210> SEQ ID NO 43
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 43

```
taatccctag ccactatgcg t                                              21
```

<210> SEQ ID NO 44
<211> LENGTH: 48
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 44

```
agcggataac aatttcacac aggaaacagc tatgacctga ggcggacg                 48
```

<210> SEQ ID NO 45
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 45

```
cgctgtctct ccgatggc                                                  18
```

<210> SEQ ID NO 46
<211> LENGTH: 51
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 46

```
agcggataac aatttcacac aggaaacagc tatgaccagc tcagtcttct c             51
```

<210> SEQ ID NO 47
<211> LENGTH: 13
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 47

```
gcgcccgcca tgg                                                       13
```

<210> SEQ ID NO 48
<211> LENGTH: 51
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 48

```
agcggataac aatttcacac aggaaacagc tatgacggcg atatcatcat c             51
```

<210> SEQ ID NO 49
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 49

```
cgccagctca ccatgga                                                   17
```

```
<210> SEQ ID NO 50
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 50
agcggataac aatttcacac agg                                              23

<210> SEQ ID NO 51
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 51
agcggataac aatttcacac aggaaacagc tatgac                                36
```

METHODS FOR MEASURING RNA TRANSLATION RATES

CROSS-REFERENCE TO RELATED APPLICATIONS

This application claims the benefit of U.S. Provisional Application No. 62/355,122, filed on 27 Jun. 2016; the entire contents of said application are incorporated herein in their entirety by this reference.

STATEMENT OF RIGHTS

This invention was made with government support under grant number P50 CA168504 awarded by The National Institutes of Health. The government has certain rights in the invention.

BACKGROUND OF THE INVENTION

Gene expression analyses have heretofore focused on detecting the amount of nucleic acids associated with the expression of genes due to the relative ease of isolating, amplifying, and quantifying nucleic acid species. For example, large-scale analysis of mRNA molecules expressed by a cell at a given time and/or cellular state (i.e., the transcriptome) is routinely performed in a cost-, labor-, and time-effective manner due to the ready availability of chemical, enzymatic, amplification, hybridization, sequencing, and other techniques for detecting nucleic acids. However, it is increasingly becoming appreciated that determining the translation state of nucleic acids (i.e., the translatome), such as mRNAs, within a cell is a far more accurate assay for determining gene expression profiles because there is a stronger correlation between the translatome and the protein products of gene expression (i.e., the proteome) as compared to the correlation between the transcriptome and the proteome (see, for example, U.S. Pat. Nos. 6,013,437 and 8,486,865; Ingolia (2016) *Cell* 165:22-33; King et al. (2016) *Brief Funct. Genomics* 15:22-31; Brar and Weissman (2015) *Nat. Rev. Mol. Cell Biol.* 16:651-664; Kitchen et al. (2014) *Nat. Neurosci.* 17:1491-1499; Gawron et al. (2014) *Proteomics* 14:2647-2662; Kuersten et al. (2013) *Wiley Interdiscip. Rev. RNA* 4:617-630); Thoreen et al. (2012) *Nature* 485:109-113; and Ingolia et al. (2011) *Cell* 147:789-802). Nevertheless, known methods for translatome analysis, such as polysome profiling and ribosome profiling, are time-consuming, expensive, laborious, and generally require highly specific instruments and reagents (see, for example, U.S. Pat. Nos. 6,013,437 and 8,486,865; Ingolia et al. (2012) *Nat. Protoc.* 7:1534-1550; Ingolia et al. (2009) *Science* 324:218-223; Gao et al. (2015) *Nat. Methods* 12:147-153; Lee et al. (2012) *Proc. Natl. Acad. Sci. USA* 109:E2424-E2432; Gandin et al. (2014) *J. Vis. Exp.* 87:51455; Esposito et al. (2010) *J. Vis. Exp.* 40:1948; and Benes and Castoldi (2010) *Methods* 50:244-249). Thus, a great need exists for methods to rapidly generate nucleic acid translation rate determinations in a cost-effective and labor-effective manner that does not necessitate the use of highly specialized instruments or reagents.

SUMMARY OF THE INVENTION

The present invention overcomes the long-felt difficulties in determining nucleic acid translation rates in a cost-, labor-, and time-effective manner that does not necessitate the use of highly specialized instruments or reagents using methods referred to as "Targeted Profiling of Translation Rate" (TPTR) methods.

In one aspect, a method of determining the abundance of target RNA bound to ribosomes within a population of RNA-ribosome complexes, comprising: a) generating a population of RNA fragments protected from degradation by an agent that degrades nucleic acids that are not protected by a ribosome by i) contacting the population of RNA-ribosome complexes with an agent that preferentially pauses the ribosomes at one or more defined regions of the RNA molecules for a sufficient time to pause the ribosomes at the one or more defined regions of the RNA molecules, and ii) contacting the population of RNA-ribosome complexes with an agent that degrades nucleic acids that are not protected by a ribosome; b) converting the undegraded RNA into complementary DNA (cDNA) using reverse transcriptase and at least 2 reverse transcription primers, wherein i) the 3' portion of each of the at least 2 reverse transcription primers has a sequence that is substantially complementary to the one or more defined regions of the RNA molecule or molecules within the population of RNA-ribosome complexes and anneals with the one or more defined regions of the RNA molecule or molecules at or above the active temperature of the reverse transcriptase, ii) the 5' portion of the at least 2 reverse transcription primers has a sequence that is substantially identical to the 3' portion of a reverse amplification primer of step c), and iii) each of the at least 2 reverse transcription primers is at least about 6 nucleotides in length; c) amplifying the cDNA with polymerase chain reaction (PCR) using a forward and a reverse amplification primer and DNA polymerase to form a detectable number of amplified cDNA of a defined region of a target RNA, wherein i) the 3' portion of the forward amplification primer has a sequence that is substantially complementary to a region that is more 3' of the cDNA as compared with the sequence of the corresponding reverse transcription primer and anneals with the cDNA at or above the active temperature of the DNA polymerase; ii) the 3' portion of the reverse amplification primer comprises a sequence that is substantially identical to the 5' portion of the corresponding reverse transcription primer and anneals with the complementary strand of the cDNA or its amplification products formed by extension of the forward amplification primer at or above the active temperature of the DNA polymerase; and iii) the PCR product is longer than the length of the reverse transcription primers; d) repeating step c) with at least one different forward and/or reverse amplification primer to form a detectable number of amplified cDNA of a defined region of a different target RNA; and e) comparing the detected amplified cDNA of step c) to the detected amplified cDNA of step d) to determine the abundance of target RNA bound to ribosomes within the population of RNA-ribosome complexes, is provided.

Numerous embodiments are further provided that can be applied to any aspect of the present invention and/or combined with any other embodiment described herein. For example, in one embodiment, the RNA of the RNA-ribosome complexes and/or the target RNA is messenger RNA (mRNA), non-coding RNA, long non-coding RNA (lncRNA), untranslated regions of RNA (UTRs), pseudogene RNA, and combinations thereof. In another embodiment, the population of RNA-ribosome complexes is obtained by lysing cells, optionally wherein the cells are lysed with chemical(s) comprising one or more detergents, mechanical disruption, sonication, and/or freezing and thawing. In still another embodiment, the cells are in a form selected from the group consisting of cultured cells, biopsies, fresh cells, FFPE formalin-fixed paraffin-embedded (FFPE) cells, paraffinized cells, and frozen cells. In yet another embodiment, the agent that preferentially pauses the ribosomes at the one or more defined regions of the RNA molecules is cycloheximide, lactimidomycin, harringtonine, and/or derivatives thereof and combinations thereof. In another embodiment, the one or more defined regions of the RNA molecules is selected from the group consisting of a translation initiation site and a translation termination site. In still another embodiment, the time sufficient to pause the ribosomes at the one or more defined regions of the RNA molecules is at least 5 seconds. In yet another embodiment, the agent that degrades nucleic acids that are not protected by a ribosome is selected from the group consisting of DNases and RNases. In another embodiment, the RNA-ribosome complexes are contacted with a DNase prior to, concurrently with, or after contact with an RNase. In still another embodiment, the nucleic acids that are not protected by a ribosome are mRNA, non-coding RNA, long non-coding RNA (lncRNA), untranslated regions of RNA (UTRs), pseudogene RNA, and combinations thereof. In yet another embodiment, the nucleic acids that are not protected by a ribosome are DNA and/or ribosomal RNA. In another embodiment, the RNA-ribosome complexes are contacted with the agent that preferentially pauses the ribosomes at the one or more defined regions of the RNA molecules before contact with the agent that degrades nucleic acids. In still another embodiment, the RNA-ribosome complexes are contacted with the agent that preferentially pauses the ribosomes at the one or more defined regions of the RNA molecules at the same time as the agent that degrades nucleic acids. In yet another embodiment, the population of RNA fragments protected from degradation is purified prior to converting to cDNA. In another embodiment, the 3' portion of each of the at least 2 reverse transcription primers that is substantially complementary to the one or more defined regions of the RNA molecule or molecules within the population of RNA-ribosome complexes is within the region that is 30 nucleotides upstream and 30 nucleotides downstream of the one or more defined regions. In still another embodiment, the substantially complementary region is within the region that is 20 nucleotides upstream and 20 nucleotides downstream of the one or more defined regions. In yet another embodiment, the substantially complementary region is within the region that is 15 nucleotides upstream and 15 nucleotides downstream of the one or more defined regions. In another embodiment, the 3' portion of each of the at least 2 reverse transcription primers has a sequence that is substantially complementary to the one or more defined regions of the RNA molecule or molecules within the population of RNA-ribosome complexes and has a sequence and/or length to anneal with the one or more defined regions of the RNA molecule or molecules at or above the active temperature of the reverse transcriptase, optionally wherein the 3' portion is the 3' end of the at least 2 reverse transcription primers. In still another embodiment, the 5' portion of the at least 2 reverse transcription primers has a sequence that is substantially identical to the 3' portion of a reverse amplification primer of step c), optionally wherein the 5' portion is the 5' end of the at least 2 reverse transcription primers. In yet another embodiment, the 5' portion of the at least 2 reverse transcription primers has a sequence that is substantially identical to the 3' portion of a reverse amplification primer of step c) has a common sequence among the at least 2 reverse transcription primers for binding the reverse amplification primer of step c). In another embodiment, the RNA binding regions of the at least 2 reverse transcription primers are sufficiently long to bind reverse transcriptase. In still another embodiment, the at least 2 reverse transcription primers specifically bind cDNA converted from the target RNA. In yet another embodiment, the active temperature of the reverse transcriptase is between about 40° C. and 50° C. In another embodiment, the at least 1 of the at least 2 reverse transcription primers is between about 6 and 500 nucleotides in length. In still another embodiment, the at least 1 of the at least 2 reverse transcription primers comprises a modified base and/or a modified backbone. In yet another embodiment, the modified backbone comprises methylenemorpholine rings and phosphorodiamidate linkages. In another embodiment, the at least 1 of the at least 2 reverse transcription primers comprises a detectable label. In still another embodiment, the at least 2 reverse transcription primers is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 reverse transcription primers. In yet another embodiment, the extension temperature is ramped upward during reverse transcription. In another embodiment, the PCR is real-time PCR, such as quantitative real-time PCR (qPCR). In still another embodiment, the binding regions of the forward and reverse amplification primers to the cDNA template and amplification products are sufficiently long to bind the DNA polymerase. In yet another embodiment, the forward amplification primer specifically binds cDNA converted from the target RNA and the reverse amplification primer specifically binds the complementary strand of the cDNA converted from the target RNA.

In another embodiment, the active temperature of the DNA polymerase is at least about 50° C. In still another embodiment, the at least 1 of the forward or reverse amplification primers comprises a modified base and/or a modified backbone. In yet another embodiment, the modified backbone comprises methylenemorpholine rings and phosphorodiamidate linkages. In another embodiment, at least 1 of the forward or reverse amplification primers comprises a detectable label. In still another embodiment, the detectable label(s) is one or more fluorophores, optionally wherein the fluorophore(s) is a dye whose fluorescence intensity and/or spectrum changes upon binding to double-stranded DNA or a fluorescently labeled nucleic acid probe. In yet another embodiment, the annealing and extension cycle temperature is ramped upward within each cycle during PCR amplification. In another embodiment, the amplified cDNA is not sequenced. In still another embodiment, the cDNA and/or amplified cDNA is not used to produce a cDNA library. In yet another embodiment, the RNA-ribosome complexes, undegraded RNA, cDNA, and/or amplified cDNA is not size-selected on a gradient or gel.

In another aspect, a method of determining the abundance of target RNA bound to ribosomes within a population of RNA-ribosome complexes, comprising: a) generating a population of RNA fragments protected from degradation by an agent that degrades nucleic acids that are not protected by a ribosome by i) contacting the population of RNA-ribosome complexes with an agent that preferentially pauses the ribosomes at one or more defined regions of the RNA molecules for a sufficient time to pause the ribosomes at the one or more defined regions of the RNA molecules, and ii) contacting the population of RNA-ribosome complexes with an agent that degrades nucleic acids that are not protected by a ribosome; b) converting the undegraded RNA into complementary DNA (cDNA) using reverse transcriptase and at least 1 reverse transcription primer, wherein i) the 3' portion of each of the at least 1 reverse transcription primer has a sequence that is substantially complementary to the one or more defined regions of the RNA molecule or molecules within the population of RNA-ribosome complexes and anneals with the one or more defined regions of the RNA molecule or molecules at or above the active temperature of the reverse transcriptase, ii) the 5' portion of the at least 1 reverse transcription primer has a sequence that is substantially identical to the 3' portion of a reverse amplification primer of step c), and iii) the at least 1 reverse transcription primer is at least about 6 nucleotides in length; c) amplifying the cDNA with polymerase chain reaction (PCR) using a forward and a reverse amplification primer to form a detectable number of amplified cDNA of a defined region of a target RNA, wherein i) the 3' portion of the forward amplification primer has a sequence that is substantially complementary to a region that is more 3' of the cDNA as compared with the sequence of the reverse transcription primer and anneals with the cDNA at or above the active temperature of the DNA polymerase; ii) the 3' portion of the reverse amplification primer comprises a sequence that is identical to the 5' portion of the reverse transcription primer and anneals with the complementary strand of the cDNA or its amplification products formed by extension of the forward amplification primer at or above the active temperature of the DNA polymerase; and iii) the PCR product is longer than the length of the reverse transcription primer; d) repeating steps b) and c) with at least one different reverse transcription primer and at least 1 different forward and/or reverse amplification primer to form a detectable number of amplified cDNA of a defined region of a different target RNA; and e) comparing the detected amplified cDNA of step c) to the detected amplified cDNA of step d) to determine the abundance of target RNA bound to ribosomes within the population of RNA-ribosome complexes, is provided.

As described above, numerous embodiments are further provided that can be applied to any aspect of the present invention and/or combined with any other embodiment described herein. For example, in one embodiment, steps b) and c) are performed in the same vessel. In another embodiment, the reverse transcriptase of step b) is heat inactivated before or during step c) and the DNA polymerase in step c) is heat activated. In still another embodiment, the RNA of the RNA-ribosome complexes and/or the target RNA is messenger RNA (mRNA), non-coding RNA, long non-coding RNA (lncRNA), untranslated regions of RNA (UTRs), pseudogene RNA, and combinations thereof. In yet another embodiment, the population of RNA-ribosome complexes is obtained by lysing cells, optionally wherein the cells are lysed with chemical(s) comprising one or more detergents, mechanical disruption, sonication, and/or freezing and thawing. In another embodiment, the cells are in a form selected from the group consisting of cultured cells, biopsies, fresh cells, FFPE formalin-fixed paraffin-embedded (FFPE) cells, paraffinized cells, and frozen cells. In still another embodiment, the agent that preferentially pauses the ribosomes at the one or more defined regions of the RNA molecules is selected from the group consisting of cycloheximide, lactimidomycin, harringtonine, and/or derivatives thereof and combinations thereof. In yet another embodiment, the one or more defined regions of the RNA molecules is selected from the group consisting of a translation initiation site and a translation termination site. In another embodiment, the time sufficient to pause the ribosomes at the one or more defined regions of the RNA molecules is at least 5 seconds. In still another embodiment, the agent that degrades nucleic acids that are not protected by a ribosome is selected from the group consisting of DNases and RNases. In yet another embodiment, the RNA-ribosome complexes are contacted with a DNase prior to, concurrently with, or after contact with an RNase. In another embodiment, the nucleic acids that are not protected by a ribosome are mRNA, non-coding RNA, long non-coding RNA (lncRNA), untranslated regions of RNA (UTRs), pseudogene RNA, and combinations thereof. In still another embodiment, the nucleic acids that are not protected by a ribosome are DNA and/or ribosomal RNA. In yet another embodiment, the RNA-ribosome complexes are contacted with the agent that preferentially pauses the ribosomes at the one or more defined regions of the RNA molecules before contact with the agent that degrades nucleic acids. In another embodiment, the RNA-ribosome complexes are contacted with the agent that preferentially pauses the ribosomes at the one or more defined regions of the RNA molecules at the same time as the agent that degrades nucleic acids. In still another embodiment, the population of RNA fragments protected from degradation is purified prior to converting to cDNA. In yet another embodiment, the 3' portion of each of the at least 1 reverse transcription primers that is substantially complementary to the one or more defined regions of the RNA molecule or molecules within the population of RNA-ribosome complexes is within the region that is 30 nucleotides upstream and 30 nucleotides downstream of the one or more defined regions. In another embodiment, the substantially complementary region is within the region that is 20 nucleotides upstream and 20 nucleotides downstream of the one or more defined regions. In still another embodiment, the substantially complementary region is within the region that is 15 nucleotides upstream and 15 nucleotides downstream of the one or more defined regions. In yet another embodiment, the 3' portion of each of the at least 1 reverse transcription primers has a sequence that is substantially complementary to the one or more defined regions of the RNA molecule or molecules within the population of RNA-ribosome complexes and has a sequence and/or length to anneal with the one or more defined regions of the RNA molecule or molecules at or above the active temperature of the reverse transcriptase is the 3' end of the at least 1 reverse transcription primers.

In another embodiment, the 5' portion of the at least 1 reverse transcription primers has a sequence that is substantially identical to the 3' portion of a reverse amplification primer of step c) is the 5' end of the at least 1 reverse transcription primers. In still another embodiment, the 5' portion of the at least 1 reverse transcription primers has a sequence that is substantially identical to the 3' portion of a reverse amplification primer of step c) has a common sequence among the at least 1 reverse transcription primers for binding the reverse amplification primer of step c). In yet another embodiment, the RNA binding regions of the at least 1 reverse transcription primers are sufficiently long to bind reverse transcriptase. In another embodiment, the at least 1 reverse transcription primers specifically bind cDNA converted from the target RNA. In still another embodiment, the active temperature of the reverse transcriptase is between about 40° C. and 50° C. In yet another embodiment, at least 1 of the at least 1 reverse transcription primers is between about 6 and 500 nucleotides in length. In another embodiment, at least 1 of the at least 1 reverse transcription primers comprises a modified base and/or a modified backbone. In still another embodiment, the modified backbone comprises methylenemorpholine rings and phosphorodiamidate linkages. In yet another embodiment, at least 1 of the at least 1 reverse transcription primers comprises a detectable label. In another embodiment, the at least 1 reverse transcription primers is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 reverse transcription primers. In still another embodiment, the extension temperature is ramped upward during reverse transcription. In yet another embodiment, the PCR is real-time PCR, such as qPCR. In another embodiment, the binding regions of the forward and reverse amplification primers to the cDNA template and amplification products are sufficiently long to bind the DNA polymerase. In still another embodiment, the forward amplification primer specifically binds cDNA converted from the target RNA and the reverse amplification primer specifically binds the complementary strand of the cDNA converted from the target RNA. In yet another embodiment, the active temperature of the DNA polymerase is at least about 50° C. In another embodiment, at least 1 of the forward or reverse amplification primers comprises a modified base and/or a modified backbone. In still another embodiment, the modified backbone comprises methylenemorpholine rings and phosphorodiamidate linkages. In yet another embodiment, at least 1 of the forward or reverse amplification primers comprises a detectable label. In another embodiment, the detectable label(s) is one or more fluorophores, optionally wherein the fluorophore(s) is a dye whose fluorescence intensity and/or spectrum changes upon binding to double-stranded DNA or a fluorescently labeled nucleic acid probe. In still another embodiment, the annealing and extension cycle temperature is ramped upward within each cycle during PCR amplification. In yet another embodiment, the amplified cDNA is not sequenced. In another embodiment, the cDNA and/or amplified cDNA is not used to produce a cDNA library. In still another embodiment, the RNA-ribosome complexes, undegraded RNA, cDNA, and/or amplified cDNA is not size-selected on a gradient or gel.

In some embodiments of any method of the present invention, the PCR product is about 20 to about 500 base pairs in length. In other embodiments of any method of the present invention, the PCR product is about 50 to about 150 base pairs in length. In still other embodiments of any method of the present invention, the abundance of target RNA bound to ribosomes within a population of RNA-ribosome complexes indicates the translation rate of the target RNA.

BRIEF DESCRIPTION OF FIGURES

FIG. 6 provides quantitative mRNA translation fold change data for the information shown in FIGS. 3 and 4.

DETAILED DESCRIPTION OF THE INVENTION

Figure 1:
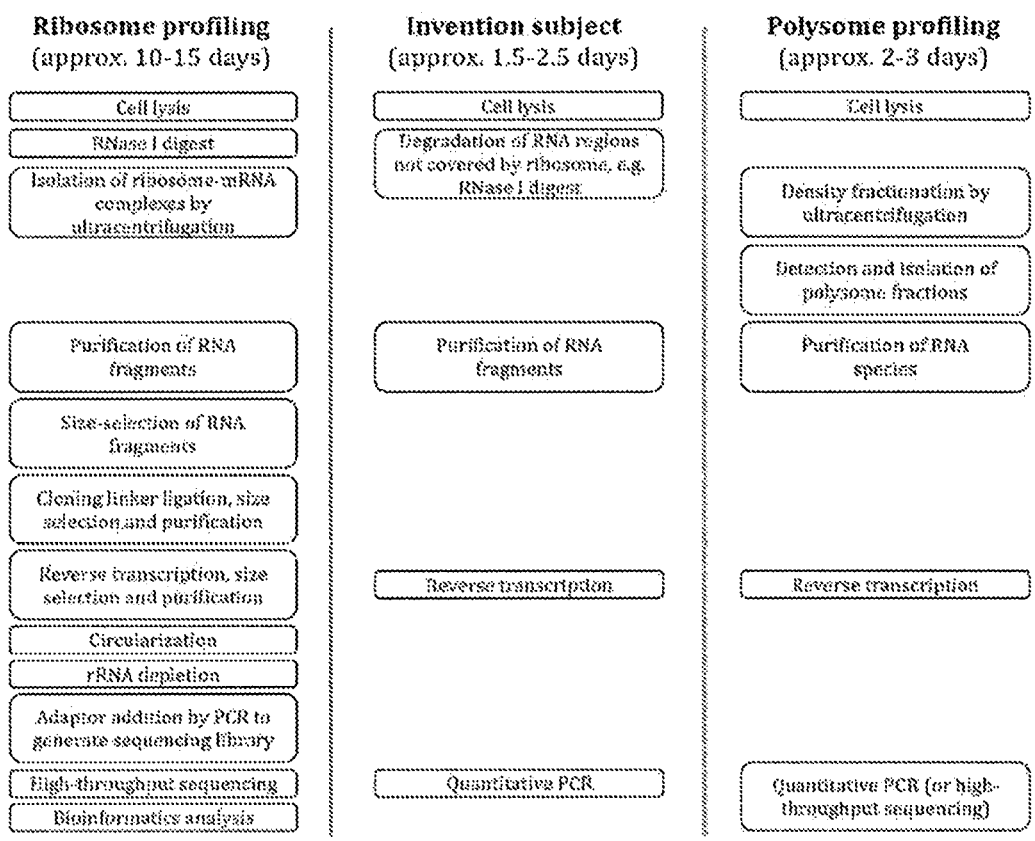
FIG. 1 shows a diagram comparing the steps of the present invention against ribosome profiling and polysome profiling methods.

The present invention provides, in part, methods for measuring RNA-to-protein translation rates in a targeted manner against specific genes of interest using methods referred to as "Targeted Profiling of Translation Rate (TPTR)" methods. Generally, the TPTR methods of the present invention involve ribosome-RNA complexes, such as those present in a cell lysate, that are treated to cause ribosome pausing on RNA species, such that there is enrichment at a defined region such as the translation initiation site, wherein the abundance at this region is correlative with the translation rate of the respective gene.

Indeed, established techniques like ribosome profiling and polysome profiling clearly demonstrate that the amount of RNA detected in association with a ribosome correlates with the translational activity of the ribosome such that more ribosomes associated with an RNA or a sequence thereof directly indicates a higher level of translational activity. Any nucleic acid regions not covered by ribosomes, such as mRNA, ribosomal RNA, genomic DNA, and the like, are degraded and degradation-resistant RNA fragments are transformed to complementary DNA (cDNA). The abundance of those fragments originating from pre-defined genes of interest can be quantified, such as by quantitative polymerase chain reaction (qPCR), as a readout of the translation rate of these genes. Reverse transcription and/or qPCR steps in the methods are designed to act specifically on those fragments containing the defined region enriched by the ribosome pausing agent.

The present invention has a number of unexpected advantages. For example, methods described herein allow translation rate determinations in a time-, cost-, and labor-effective manner without necessitating highly specialized instruments and/or reagents. In addition, the use of ribosome pausing to cause enrichment of ribosomes at defined region(s) is believed to improve the fidelity of reverse transcription and qPCR, while maintaining the correlation between its abundance at this region with the translation rate of the respective genes. The design of gene-specific reverse-transcription and PCR primers against such regions overcomes the challenges of detecting and/or amplifying small nucleic acid species with sufficient signal while maintaining the correlation between abundance and gene translation rates and overcoming primer-dimer problems. Finally, the methods remove the need for gel-based size selection of RNA fragments, library generation, and sequencing in ribosome profiling, as informed by a probability-based mathematical model described below, as well as the removal of the need for gradient-based lysate fractionation that occurs in polysome profiling.

A. Generating Ribosome-Protected RNA The methods described herein are useful in determining the abundance of target RNA bound to ribosomes within a population of RNA-ribosome complexes. The term "ribosome" refers to the well-known ribonucleoprotein particle having a small and large subunit that translates RNA into protein during protein synthesis. A protein is formed by the linkage of multiple amino acids via peptide bonds, according to a sequence defined by the template messenger RNA (mRNA). In bacteria these subunits have sedimentation coefficients of 30 and 50, and thus are referred to as "30S" and "50S" subunits, respectively. In eukaryotes, the sedimentation coefficients are 40 and 60. Although the ribosome in association with RNA to be translated, known as an "RNA-ribosome complex," is the central structural component of translation, the term can further encompass any one or more of a large number of additional components, including inter alia initiation, elongation, termination and recycling factors, transfer RNA, amino acids, aminoacyl synthetases, magnesium, and the product polypeptides, that mediate translation.

RNA translation, also referred to as "polypeptide synthesis", involves the stages of initiation, elongation and termination. The initiation stage begins by formation of the initiation complex, composed of the two ribosomal subunits, protein initiation factors, mRNA, and an initiator tRNA, which recognizes the initiator codon AUG of open reading frames. Elongation proceeds with repeated cycles of charged tRNAs binding to the ribosome (a step termed "recognition"), peptide bond formation, and translocation, involving elongation factors and enzymes such as peptidyl transferase, which catalyzes addition of amino acid moieties onto the growing chain. Termination factors recognize a stop signal, such as the base sequence UGA, in the mRNA, terminating polypeptide synthesis and releasing the polypeptide chain and mRNA from the ribosome. Recycling factor enables dissociation of the ribosome subunits, which are then available for a new round of protein synthesis (see, for example, Kapp et al. (2004) *Annu. Rev. Biochem.* 73:657-704). In eukaryotes, ribosomes are often attached to the membranes of the endoplasmic reticulum (ER) and Golgi compartments. Additionally, ribosomes are active in organelles such as mitochondria and, in plant cells, in chloroplasts, and in other subcellular compartments.

Many nucleic acid molecule types exist within cells and certain types, such as mRNA, are associated with a ribosome. The term "nucleic acid molecules" or "nucleic acids" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. The terms "ribonucleic acid" and "RNA" as used herein mean a polymer composed of ribonucleotides. The terms "deoxyribonucleic acid" and "DNA" as used herein mean a polymer composed of deoxyribonucleotides. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. In one embodiment, nucleic acid molecules are genomic DNA or are derived from genomic DNA, such as fragments or chromosomes. Such genomic DNA can comprise exome DNA, i.e., a subset of whole genomic DNA enriched for transcribed sequences which contains the set of exons in a genome. In further embodiments, the target nucleic acids comprise a transcriptome (i.e., the set of all mRNA or "transcripts" in a nucleic acid population, such as in a cell or population of cells), a translatome (i.e., the set of all mRNA or "transcripts" translated into protein in a nucleic acid population, such as in a cell or population of cells), a methylome (i.e., the population of methylated sites and the pattern of methylation in a genome), a phosphorylome, and the like.

Many types of RNA are known in the art, including mRNA, pre-mRNA, ribosomal RNA (rRNA), transfer RNA (tRNA), hnRNA, snRNA, non-coding RNA (e.g., small non-coding RNAs like miRNAs, pre-miRNAs, pri-miRNAs, miRNA*, anti-miRNA, and PIWI RNAs and long non-coding RNAs (lnRNAs)), and the like. As described below, the methods described herein involve the degradation of nucleic acids, including genomic DNA, small RNAs, and the like, that are not associated with a ribosome and/or are not protected from degradation by the association with the ribosome.

RNA-ribosome complexes for use in the methods of the present invention can be derived using well-known methods in the art. In some embodiments, the RNA-ribosome complexes are generated in vitro, such as by using recombinant or reconstituted RNA and ribosomal proteins. In other embodiments, the RNA-ribosome complexes are obtained from biological sources in the form of samples comprising such complexes. In either case, the term "sample" is used herein in a broad sense and is intended to include a variety of sources and compositions that contain RNA-ribosome complexes. Thus, the sample may be a biological sample, but the term also includes other, for example, artificial samples which comprise nucleic acids. Exemplary samples include, but are not limited to, whole blood; blood products such as plasma or serum; red blood cells; white blood cells; buffy coat; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; tissues, including but not limited to, liver, spleen, kidney, lung, intestine, brain, heart, muscle, pancreas, cell cultures, plant tissues or samples, as well as lysates, extracts, or materials and fractions obtained from the samples described above or any cells and microorganisms and viruses that may be present on or in a sample and the like. Materials obtained from clinical or forensic settings that contain nucleic acids are also within the intended meaning of the term "sample." In one embodiment, nucleic acid sources from biological sources, such as subjects, having a particular condition, such as cancer, and/or treated under a particular condition, such as with a therapeutic or modulator of a biological process, can be used. Non-limiting examples of such samples include frozen tissue samples, fresh tissue samples, paraffin-embedded samples, and samples that have been preserved, e.g. formalin-fixed and paraffin-embedded (FFPE samples) or other samples that were treated with cross-linking fixatives such as, for example, glutaraldehyde.

As described above, the term "sample" also includes processed samples such as preserved, fixed and/or stabilized samples. As described herein, suitable samples useful for extracting nucleic acid molecules to be fragmented according to the methods of the present invention described herein can contain biological material retrieved from a host organism of 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or longer before the methods of the present invention are applied.

The methods according to the present invention are particularly useful for generating RNA translation determinations using RNA-ribosome complexes from tissue samples, whole tissue, whole organ, bodily fluids, tumor dissections, cell culture, cell lysate, cell extract, and the like. In some embodiments, the biological sample comprises or is obtained from a "population of cells," which term indicates at least two cells.

Moreover, in some embodiments, biological samples and/or the RNA-ribosome complexes therein can be pooled in any combination of interest, such as pooling of cells of the same type and/or after the same treatment, pooling of cells of different types and/or different treatment, and the like.

For those embodiments where biological samples are used to obtain the RNA-ribosome complexes, such as whole cells or tissue samples, it is generally useful to extract the RNA-ribosome complexes from other biological material in order to generate a population of RNA-ribosome complexes for analysis. Accordingly, following sample collection, RNA-ribosome complexes may be liberated from the collected cells, biological fluids, etc., into a crude extract, followed by additional treatments to prepare the sample for subsequent operations, e.g., removal of nucleic acids unprotected by a ribosome, purification, filtration, desalting, and the like.

Liberation of RNA-ribosome complexes from the biological sample can be performed using well-known chemical, physical, or electrolytic lysis methods. For example, chemical methods generally employ lysing agents to disrupt the cells and extract the RNA-ribosome complexes from the cells. Generally, where chemical extraction and/or denaturation methods are used, the appropriate reagents may be incorporated through external introduction of agents to the sample.

Alternatively, physical methods may be used to extract the nucleic acids and denature DNA binding proteins. For example, U.S. Pat. No. 5,304,487 discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., using mechanical disruption, employing a channel with restricted cross-sectional dimension which causes cell lysis when the sample is passed through the channel with sufficient flow pressure, and the like.

In some embodiments, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to effect cell lysis/extraction, including, e.g., subjecting cells to ultrasonic agitation, freeze-thawing, trituration, or forcing cells through microgeometry apertures, thereby subjecting the cells to high shear stress resulting in rupture.

Following extraction, RNA-ribosome complexes can, but need not, be separated from other elements of the crude extract, e.g., denatured proteins, cell membrane particles, salts, and the like. Removal of particulate matter is generally accomplished by centrifugation, filtration, flocculation, or the like. A variety of filter types may be readily incorporated into the device. Further, where chemical denaturing methods are used, it may be desirable to desalt the sample prior to proceeding to subsequent steps. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like.

Alternatively, desalting methods may generally take advantage of the high electrophoretic mobility and negative charge of DNA compared to other elements.

Electrophoretic methods may also be utilized in the purification of nucleic acids from other cell contaminants and debris. In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include, e.g., dialysis membranes, dense gels, PEI filters, or other suitable materials. Upon application of an appropriate electric field, the nucleic acids present in the sample will migrate toward the positive electrode and become trapped on the capture membrane.

Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use.

In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

In some embodiments, it may be desirable to extract certain species of nucleic acids, such as DNA or RNA, species based on size (e.g., genomic, plasmid, transcribed, small, micro, chromosomal, etc.), species based on strandedness (e.g., single stranded or double stranded), species based on composition (e.g., cDNA or cRNA), and the like. Conventional techniques for isolating desired nucleic acids can be used and are well known in the art for example as disclosed in Sambrook and Russell, Molecular Cloning: A Laboratory Manual and as described in the Examples.

Non-limiting, exemplary techniques include methods of using a cartridge supported with a nucleic acid-adsorbable membrane of silica, cellulose compound, or the like, precipitation with ethanol or precipitation with isopropanol, extraction with phenol-chloroform, and the like. Furthermore, there may be mentioned methods with solid-phase extraction cartridge, chromatography, and the like using ion-exchange resins, silica supports bonded with a hydrophobic substituent such as an octadecyl group, resins having a size-exclusion effect.

The methods of the present invention are robust, such that sample(s) may be subjected to more than one type and/or a repetition of a perturbation to a biological sample to obtain suitable RNA-ribosome complexes for analysis as needed. For example, chemical (e.g., detergent) lysis of cells may be sufficient to release suitable RNA-ribosome complexes for analysis without the addition of additional manipulations, such as extensive fluid washing, mechanical disruption, sonication, freezing and thawing, trituration, and the like.

RNA-ribosome complexes for use in the methods of the present invention, whether purified, present within a semi-purified form, or present within a biological sample (e.g., within cells), are treated such that one or more ribosomes preferentially pause at one or more defined regions of an RNA molecule. Generally, the ribosome-pausing agent causes ribosome enrichment at defined regions, such that the extent of enrichment is correlative with translation rate of the respective genes. Quantitation of the abundance of these enriched regions is preferred, compared to non-enriched regions, due to greater baseline template abundance before nucleic acid amplification, such as quantitative PCR (qPCR) amplification, and hence better quantitation reliability. As described further below, reverse transcription and nucleic acid amplification primers are designed specifically against the sequence of the enriched region of genes of interest.

Many ribosome-pausing agents that preferentially pause the ribosome at one or more defined regions of an RNA molecule are known in the art. For example, cycloheximide (CHX) and lactimidomycin (LTM) (see, for example, U.S. Pat. Publ. 2013/0096012; and King and Gerber (2016) *Brief Funct. Genomics* 15:22-31). The term "pause" with respect to ribosome positioning refers to physical stabilization of a ribosome at a particular sequence and/or spatial orientation of an RNA. The term "preferential" with respect to ribosome positioning refers to the statistically significant enrichment of ribosomes paused at one or more defined regions of an RNA molecule relative to the statistically random distribution of ribosomes along all possible regions of the RNA molecule. In some embodiments, statistical significance can be measured using p-values, such as measuring the observation of RNA positions occupied by a ribosome in the presence of a ribosome pausing agent relative to that in the absence of a ribosome pausing agent with a p-value of 0.5, 0.4, 0.3, 0.2, 0.1, 0.09, 0.08, 0.07, 0.06, 0.05, 0.04, 0.03, 0.02, 0.01, or less, such as p<0.05. Any number of well-known statistical tests can be used, such as Student's t-test. For example, CHX and LTM preferentially stabilize ribosomes on translation initiation sites and at least CHX also preferentially stabilizes ribosomes on translation termination sites. In addition, harringtonine specifically pauses ribosomes at translation initiation sites. Thus, for example, a population of RNA-ribosome complexes in the presence of CHX will demonstrate a statistically significant increase in the number of ribosomes paused at the translation initiation site (e.g., a start codon) and in the number of ribosomes paused at the translation termination site (e.g., stop codon). Chemical derivatives of such compounds, such as homoharringtonine, that are also associated with ribosome pausing are also contemplated for use according to the methods of the present invention. Any known translation scanning, initiation, elongation, or termination pausing agent that does not cause ribosome separation from RNA is also contemplated for use according to the methods of the present invention.

In particular, it is known that CHX binds to the exit (E)-site of the large ribosomal subunit and close to the position where the 3' hydroxyl group of the deacylated tRNA normally binds to thereby prevent the release of deacylated tRNA from the (E)-site and blocks subsequent ribosomal translocation (U.S. Pat. Publ. 2013/0096012; Schneider-Poetsch et al. (2010) *Nat. Chem. Biol.* 6:209-217; and Klinge et al. (2011) *Science* 334:941-948). Thus, CHX causes ribosome pausing during peptide elongation and not during 5' UTR scanning such that ribosomes accumulate at the translation initiation site. It is also known that LTM preferentially acts on an initiating ribosome in a different mechanism than CHX because LTM does not bind to the (E)-site when a deacylated tRNA is present, but rather, binds only during the initiation step, in which the initiator tRNA directly enters into the peptidyl (P)-site and the empty (E)-site accessible to LTM (Ju et al. (2009) *J. Am. Chem. Soc.* 131:1370-1371; Sugawara et al. (1992) *J. Antibiot.* 45:1433-1441; Schneider-Poetsch et al. (2010) *Nat. Chem. Biol.* 6:209-217; and Steitz (2008) *Nat. Rev. Mol. Cell Biol.* 9:242-253).

In some embodiments, general ribosome pausing agents can be used to cause global enrichment of ribosomes positioned over actively translated RNAs. In sufficient quantities and in combination with the RNA amplification techniques described herein, targeted analysis of RNA regions of interest may still be detectable in the absence of specific enrichment of one or more RNA regions of interest relative to other regions of the RNA also harboring a ribosome. For example, emetine and chloramphenicol are well-known ribosome pausing agents. Similarly, ribosomes can be stabilized on regions of translated RNAs through cross-linking. The term "cross-linking" refers to the covalent binding of molecules. Agents for carrying out cross-linking are well-known in the art and include, for example, physical means, such as heat or ultraviolet radiation, and chemical means, such as the application of formaldehyde, paraformaldehyde, or other known chemical cross-linking agents.

RNA-ribosome complexes can be contacted with the one or more ribosome pausing agents either before and/or concurrently with any biological sample lysis agents. Similarly, the RNA-ribosome complexes can be contacted with the one or more ribosome pausing agents either before and/or concurrently with nucleic acid degradation agents. The RNA-ribosome complexes are contacted with the one or more ribosome pausing agents for a sufficient length of time to pause the ribosome. The length of time for such contact can be, without limitation, about 5 seconds, 10 seconds, 15 seconds, 20 seconds, 25 seconds, 30 seconds, 35 seconds, 40 seconds, 45 seconds, 50 seconds, 1 minute, 2 minutes, 3 minutes, 4 minutes, 5 minutes, 6 minutes, 7 minutes, 8 minutes, 9 minutes, 10 minutes, or longer, or any range in between, inclusive, such as about 15 seconds to about 3 minutes.

As used herein, the term "about," unless otherwise specified, refers to a recited value and a range of the recited value plus or minus 10%. In some embodiments, the range can be within 9%, 8%, 7%, 6%, 5%, 4%, 3%, 2%, 1%, or less of the recited value.

The RNA-ribosome complexes in which the ribosomes are paused and possibly enriched at one or more defined regions of the bound RNA are also contacted with a nucleic acid degradation agent. The nucleic acid degradation agent degrades nucleic acids that are not sterically protected by the bound ribosome and preserves RNA that is sterically protected by the bound ribosome. Numerous nucleic acid degradation treatments are known in the art, including thermal degradation, acid hydrolysis, and enzymatic digestion.

For example, thermodegradation involves heat-based fragmentation of nucleic acids. In one embodiment, temperatures of 80° C., 85° C., 90° C., 91° C., 92° C., 93° C., 94° C., 95° C., 96° C., 97° C., 98° C., 99° C., 100° C. or higher can be used. Incubation times can range on the order of seconds to minutes to hours. For mechanical crushing-based fragmentation, a method of cleaving the nucleic acid using balls of glass, stainless steel, zirconia, or the like can be used. Generally, degradation of polynucleotide molecules by mechanical means (e.g., nebulization, sonication and HydroShear® methods) results in fragments with a heterogeneous mix of blunt and 3'- and 5'-overhanging ends. In some embodiments, it may be desirable to repair the fragment ends using methods or kits (such as the Lucigen DNA terminator End Repair Kit™) known in the art to generate ends that are optimal for insertion, for example, into blunt sites of cloning vectors.

In one embodiment, enzymatic degradation is used, which involves the use of nucleic acid cleavage enzymes, such as an endodeoxyribonuclease DNase, such as DNase I; an exodeoxyribonuclease, such as exodeoxyribonuclease I, III, 6, and 8; an endoribonuclease, such as RNase A, H. III, L, P, PhyM, T1, T2 U2, and V; and an exoribonuclease, such as PNPase, RNase PH, R, D, T, oligoribonuclease, exoribonuclease I, and exoribonuclease II; or any combination thereof. For example, when genomic DNA and exposed RNA species are desired to be degraded, a combination of one or more deoxyribonucleases and one or more ribonucleases can be used. Nucleic acid degradation can be performed with enzyme quantities, incubation conditions, incubation temperatures, incubation buffers, incubation times, and incubation length such that nucleic acid molecules that are not protected by a ribosome are degraded to an average length of about 100, 99, 98, 97, 96, 95, 94, 93, 92, 91, 90, 89, 88, 87, 86, 85, 84, 83, 82, 81, 80, 79, 78, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1, or any range in between, inclusive, such as about 1 to about 20 nucleotides. In some embodiments, the methods tolerate lower efficiency in degradation, such as degradation of nucleic acids to lengths of 50-100 nucleotides, especially for genomic DNA regions of highly translated genes. It is expected that RNA molecules protected by ribosome(s) are also degraded to a length of about 25 to 35 nucleotides, such as 28, 29, or 30 nucleotides, which is the footprint of ribosome protection. In addition, there is likely to be partial degradation of the ribosome footprint such that final RNA length going into reverse transcription is greater than the footprint size. As confirmed by the mathematical model described below, such partial degradation is permissible according to the methods of the present invention.

In certain embodiments, the population of RNA fragments protected from nucleic acid degradation is purified prior to use in downstream processing. Suitable methods for nucleic acid purification are well-known and commercially available in the art (e.g., TRIzol® and RNA precipitation methods, silica column-based methods, gel purification methods, and the like) and are described above.

B. Detecting Ribosome-Protected RNA

Unlike traditional translatome profiling methods specifically requiring laborious, expensive, and time-consuming steps, such as size selection, library generation, gradient separation, the methods of the present invention detect ribosome-protected RNA using conversion to complementary DNA (cDNA) and oligonucleotide-based cDNA amplification, such as using the polymerase chain reaction (PCR) like quantitative PCR (qPCR), steps. Specifically, the ribosome-protected RNA is converted into first-strand cDNA by reverse transcription (RT) and the resulting cDNA is used as template in an oligonucleotide-based amplification and detection method.

In some embodiments, the RT, amplification, and detection steps are performed in the same vessel. In other embodiments, the RT is performed in a separate vessel from the amplification and detection steps. Both variations of the present invention are described further below.

The term "reverse transcriptase activity" and "reverse transcription" refers to the enzymatic activity of a class of polymerases characterized as RNA-dependent DNA polymerases that can synthesize a DNA strand (i.e., cDNA) using an RNA strand as a template. "Reverse transcription-PCR" or "RT-PCR" is a PCR reaction that uses RNA template and reverse transcriptase(s), or enzyme(s) having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Similarly, multiplex reverse transcription refers to reverse transcription reactions that produce more than one type of cDNA in a single reaction, typically by the inclusion of more than one reverse transcription primer in a single reaction.

Exemplary reverse transcriptases include, but are not limited to, the Moloney murine leukemia virus (M-MLV) RT as described in U.S. Pat. No. 4,943,531, a mutant form of M-MLV-RT lacking RNase H activity as described in U.S. Pat. No. 5,405,776, bovine leukemia virus (BLV) RT, Rous sarcoma virus (RSV) RT, Avian Myeloblastosis Virus (AMV) RT and reverse transcriptases disclosed in U.S. Pat. No. 7,883,871.

In some embodiments, reverse transcriptase and PCR are performed in a procedure known as reverse transcription-PCR, which can be carried out as either an end-point or real-time assay. It involves two separate molecular syntheses: (i) the synthesis of cDNA from an RNA template; and (ii) the replication of the newly synthesized cDNA through PCR amplification. In order to address the technical problems often associated with reverse transcription-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcription-PCR procedure (e.g., two-step reverse transcription-PCR), reverse transcription is performed as an independent step using the optimal buffer condition for reverse transcriptase activity. Following cDNA synthesis, the reaction is adjusted for $MgCl_2$, and deoxyribonucleoside triphosphate (dNTP) concentrations amongst other conditions to conditions optimal for DNA polymerase activity of the DNA polymerase, such as Taq polymerase, and PCR is carried out according to standard conditions (see U.S. Pat. Nos. 4,683,195 and 4,683,202). By contrast, "coupled" RT PCR methods use a common buffer optimized for reverse transcriptase and DNA polymerase activities. In one embodiment, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{2+}$ then PCR is carried out in the absence of $Mn^{2+}$ after the removal of $Mn^{2+}$ by a chelating agent. Finally, the "continuous" method (e.g., one step reverse transcription-PCR) integrates the three reverse transcription-PCR steps into a single continuous reaction that avoids the opening of the reaction tube for component or enzyme addition. Continuous reverse transcription-PCR has been described as a single enzyme system using the reverse transcriptase activity of thermostable Taq DNA polymerase and Tth polymerase and as a two enzyme system using AMV RT and Taq DNA polymerase, wherein the initial 65° C. RNA denaturation step may be omitted.

One-step reverse transcription-PCR provides several advantages over uncoupled reverse transcription-PCR. One step reverse transcription-PCR requires less handling of the reaction mixture reagents and nucleic acid products than uncoupled reverse transcription-PCR (e.g., opening of the reaction tube for component or enzyme addition in between the two reaction steps), and is therefore less labor intensive, reducing the required number of person hours. One step reverse transcription-PCR also requires less sample, and reduces the risk of contamination. The sensitivity and specificity of one-step reverse transcription-PCR has proven well suited for studying expression levels of one to several genes in a given sample. Typically, this procedure has been limited to use of gene-specific primers to initiate cDNA synthesis. In such methods, the reverse transcriptase can be heat inactivated before or during heat activation of DNA polymerase.

Regardless of whether reverse transcription, and nucleic acid amplification and/or detection, are performed independently in different vessels or continuously in the same vessel, many different types of nucleic acid amplification techniques can be used according to the oligonucleotide parameters discussed further below. For example, in some embodiments, nucleic acid amplification can be accomplished by a variety of methods. The polymerase chain reaction (PCR) and variations thereof is the method most commonly used to amplify specific target DNA sequences although, in some embodiments, other techniques like nucleic acid sequence based amplification (NASBA), ligase chain reaction (LCR), strand displacement amplification (SDA) reaction, transcription mediated amplification (TMA) reaction, and rolling circle amplification (RCA) can be used.

PCR generally refers to a method for amplification of a desired nucleotide sequence in vitro involving introducing a molar excess of two or more extendable oligonucleotide primers to a reaction mixture comprising a sample having the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers.

PCR amplification generally has three phases: exponential phase, linear phase and plateau phase. The exponential phase is the first phase of PCR amplification. During this exponential phase, reaction components are in excess. Assuming 100% reaction efficiency, there is an exact doubling of product each cycle, and the reaction is specific and precise.

The linear phase is the second phase of PCR amplification, during which the reaction components are continuously being consumed but become limiting, amplification therefore slows and the reactions become highly variable. The final phase of PCR amplification is the plateau phase. At the plateau phase, the reaction components are insufficient for amplification and very few or no products are being generated.

The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584. The term "PCR fragment" or "reverse transcription-PCR fragment" or "amplicon" refers to a polynucleotide molecule (or collectively the plurality of molecules) produced following the amplification of a particular target nucleic acid. A PCR fragment is typically, but not exclusively, a DNA PCR fragment. A PCR fragment can be single-stranded or double-stranded, or in a mixture thereof in any concentration ratio. A PCR fragment or RT-PCR fragment can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 nucleotides in length, or more, or any range in between, inclusive, such as about 20 to about 500 nucleotides in length, about 50 to about 150 nucleotides in length, etc.

A "buffer" is a compound added to an amplification reaction which modifies the stability, activity, and/or longevity of one or more components of the amplification reaction by regulating the pH of the amplification reaction. The buffering agents of the invention are compatible with PCR amplification. Certain buffering agents are well known in the art and include, but are not limited to, Tris, Tricine, MOPS (3-(N-morpholino) propanesulfonic acid), and HEPES (4-(2-hydroxyethyl)-1-piperazineethanesulfonic acid). In addition, PCR buffers may generally contain up to about 70 mM KCl and about 1.5 mM or higher $MgCl_2$, to about 50-200 mM each of nucleotides dATP, dCTP, dGTP and dTTP. The buffers of the invention may contain additives to optimize efficient reverse transcription-PCR or PCR reaction.

An additive is a compound added to a composition which modifies the stability, activity, and/or longevity of one or more components of the composition. In certain embodiments, the composition is an amplification reaction composition. In certain embodiments, an additive inactivates contaminant enzymes, stabilizes protein folding, and/or decreases aggregation. Exemplary additives that may be included in an amplification reaction include, but are not limited to, betaine, formamide, KCl, CaCl$_2$, MgOAc, MgCl$_2$, NaCl, NH$_4$OAc, NaI, Na(CO$_3$)$_2$, LiCl, MnOAc, NMP, trehalose, demethylsulfoxide ("DMSO"), glycerol, ethylene glycol, dithiothreitol ("DTT"), pyrophosphatase (including, but not limited to *Thermoplasma acidophilum* inorganic pyrophosphatase ("TAP")), bovine serum albumin ("BSA"), propylene glycol, glycinamide, CHES, Percoll™, aurintricarboxylic acid, TWEEN® 20, TWEEN® 21, TWEEN® 40, TWEEN® 60, TWEEN® 85, Brij 30, NP-40, Triton X-100, CHAPS, CHAPSO, Mackernium, LDAO (N-dodecyl-N,N-dimethylamine-N-oxide), Zwittergent 3-10, Xwittergent 3-14, Xwittergent SB 3-16, Empigen, NDSB-20, T4G32, *E. Coli* SSB, RecA, nicking endonucleases, 7-deazaG, dUTP, UNG, anionic detergents, cationic detergents, non-ionic detergents, zwittergent, sterol, osmolytes, cations, and any other chemical, protein, or cofactor that may alter the efficiency of amplification. In certain embodiments, two or more additives are included in an amplification reaction.

The term "template" or "template nucleic acid" refers to a plurality of nucleic acid molecules used as the starting material or template for amplification in a PCR reaction or reverse transcription-PCR reaction. Template nucleic acid sequences may include both naturally occurring and synthetic molecules. Exemplary template nucleic acid sequences include, but are not limited to, RNA protected from degradation by association with a ribosome.

A "target sequence", "target DNA" or "target RNA" or "target nucleic acid", or "target nucleic acid sequence" refers to a region of a template nucleic acid that is to be analyzed.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base-specific, e.g., A/T and G/C, by Watson/Crick and Hoogsteen-type hydrogen bonding. In certain embodiments, base-stacking and hydrophobic interactions may also contribute to duplex stability.

As used herein, "stringent conditions" for hybridization refer to conditions under which a nucleic acid having complementarity to a target sequence predominantly hybridizes with the target sequence, and substantially does not hybridize to non-target sequences, or, in some embodiments, sufficiently hybridizes to a target sequence of interest suitable for detection according to the methods of the present invention despite hybridizing in some fashion to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. In general, preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. For applications involving oligonucleotide binding stringencies in nucleic acid amplification reactions and where washing is not involved, such as in a reverse transcription and/or PCR assay, oligonucleotide binding stringencies are generally dependent upon temperature and high stringency binding occurs when the hybridization temperature is close to the melting temperature, such as within the ranges of melting and anneal temperatures described below.

A "DNA-dependent DNA polymerase activity" refers to the activity of a DNA polymerase enzyme that uses deoxyribonucleic acid (DNA) as a template for the synthesis of a complementary and anti-parallel DNA strand. In certain embodiments, the nucleic acid polymerase is a thermostable polymerase that may have more than one of the above-specified catalytic activities. As used herein, the term "thermostable", as applied to an enzyme, refers to an enzyme that retains its biological activity at elevated temperatures (e.g., at 55° C. or higher), or retains its biological activity following repeated cycles of heating and cooling.

As used herein, an "amplifying polymerase activity" refers to an enzymatic activity that catalyzes the polymerization of deoxyribonucleotides or ribonucleotides. Generally, the enzyme will initiate synthesis at the 3'-end of the primer annealed to a target nucleic acid template sequence, and will proceed toward the 5' end of the template strand.

Non-limiting examples of thermostable DNA polymerases may include, but are not limited to, polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus* rubber (Tru polymerase), *Thermus brockianus* (DYNAZYME™ polymerase), *Thermotoga maritime* (Tma) and other species of the *Thermotoga* genus (Tsp polymerase), and *Methanobacterium thermoautotrophicum* (Mth polymerase). The PCR reaction may contain more than one thermostable polymerase enzyme with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form.

Alternatively, the polymerase may be modified to contain a fragment of the enzyme or to contain a mutation that provides beneficial properties to facilitate the PCR reaction. In one embodiment, the thermostable polymerase may be Taq DNA polymerase. Many variants of Taq polymerase with enhanced properties are known and include, but are not limited to AmpliTaq™, AmpliTaq™, Stoffel fragment, SuperTaq™, SuperTaq™ plus, LA Taq™, LApro Taq™, and EX Taq™.

The RNA-protected RNA and corresponding cDNA generated therefrom are short nucleic acid species that are challenging to amplify, detect, and quantify using standard methods. However, it has been determined herein that the design of oligonucleotides according to particular parameters at both the reverse transcription and nucleic acid amplification stage can overcome thus challenges.

The term "oligonucleotide" refers to a nucleic acid molecule having at least 2 nucleotides covalently linked together. Oligonucleotides are typically from about 5, 6, 7, 8, 9, 10, 12, 15, 25, 30, 40, 50, 60, 70, 80, 90, 100, 150, 200, 250, 300, 350, 400, 450, or more nucleotides in length, up to about 500 nucleotides in length. Nucleic acids and polynucleotides are polymers of any length, including longer lengths, e.g., greater than 500, 1000, 2000, 3000, 5000, 7000, 10,000, etc. The term "nucleotide" typically refers to a single unit of a polynucleotide, i.e., a monomer. Nucleotides can be ribonucleotides, deoxyribonucleotides, or modified versions thereof. The term "oligonucleotide" encompasses nucleic acid primers and probes.

As used herein, the term "amplification primer" or "PCR primer" or "primer" refers to an enzymatically extendable oligonucleotide that comprises a defined sequence that is designed to hybridize in an antiparallel manner with a complementary, primer-specific portion of a target nucleic acid sequence. Thus, the primer, which is generally in molar excess relative to its target polynucleotide sequence, primes template-dependent enzymatic DNA synthesis and amplification of the target sequence. A primer nucleic acid does not need to have 100% complementarity with its template subsequence for primer elongation to occur; primers with less than 100% complementarity can be sufficient for hybridization and polymerase elongation to occur provided the penultimate base at the 3' end of the primer is able to base pair with the template nucleic acid. A PCR primer is preferably, but not necessarily, synthetic, and will generally be approximately about 10 to about 100 nucleotides in length.

The term "probe" comprises a polynucleotide that comprises a specific portion designed to hybridize in a sequence-specific manner with a complementary region of a specific nucleic acid sequence, such as a target nucleic acid sequence. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the well-known references describing real-time nucleic acid amplification techniques, such as TaqMan™ and CataCleave™ assays described in U.S. Pat. Nos. 5,763,181; 6,787,304; and 7,112,422.

Oligonucleotides may be synthesized and prepared by any suitable method (such as chemical synthesis), which is known in the art. A number of computer programs (e.g., Primer-Express) are readily available to design optimal primer sets according to the oligonucleotide design parameters described below.

Figure 2:
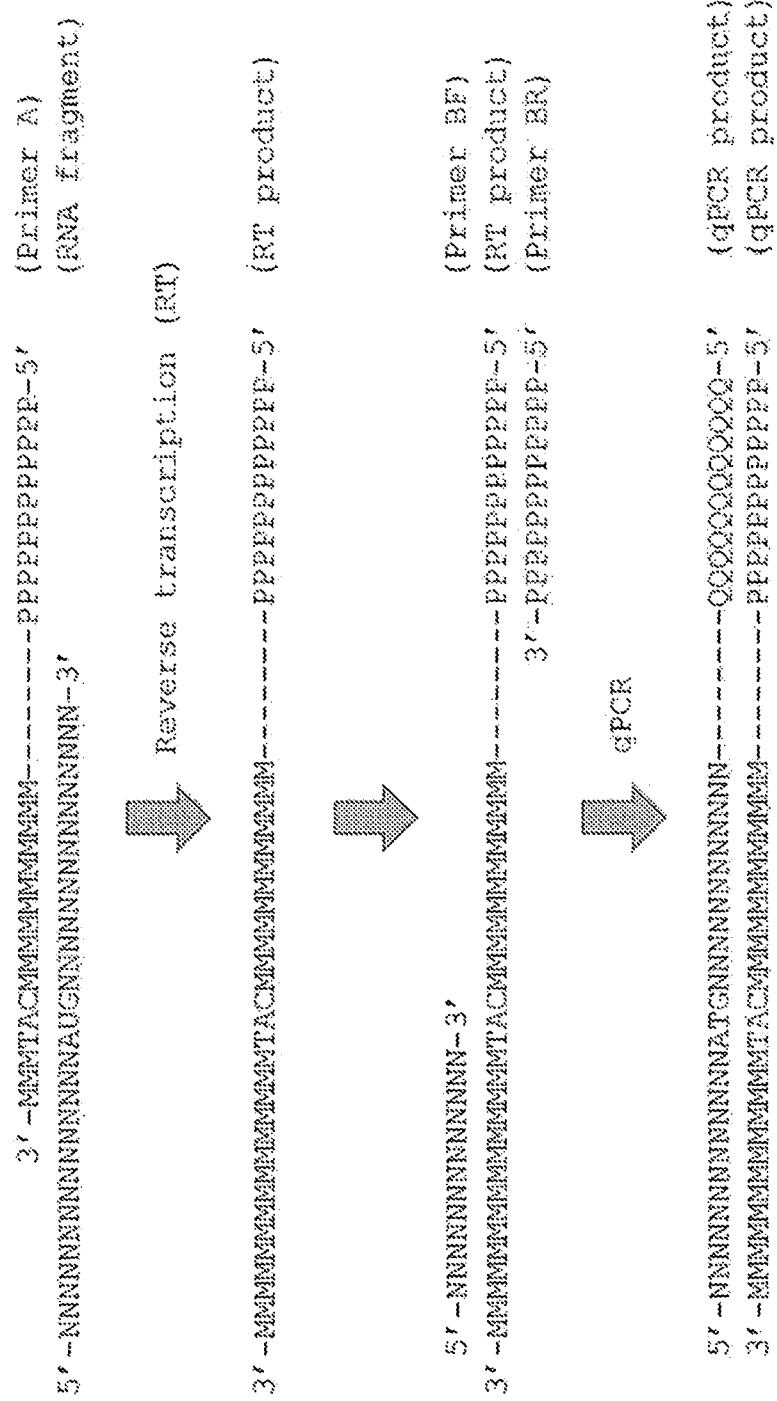
FIG. 2 shows an exemplary schematic diagram of primer design principles useful for the present invention that should not be construed as limiting.

FIG. 2 provides a non-limiting exemplary schematic description and the following illustration embodies a translation start codon as the defined region of the RNA molecule, although the same principle can be applied to any other defined region of interest corresponding to the ribosomal pausing agent (e.g., translation stop site, stem-loop structure, and the like). In addition to embodiments of the present invention shown in FIG. 2, other embodiments are contemplated and described herein, such as the use of short reverse transcription oligonucleotides in combination with long reverse and forward PCR primers.

The following general principles can be used to design oligonucleotides suitable for use according to the methods of the present invention.

Reverse transcription oligonucleotides (e.g., primer A in FIG. 2) are designed with 3' portion, alternatively referred to as a 3' region, sequences that are complementary to sequences within defined regions of ribosome enrichment. For example, the 3' region sequence is complementary to a region mostly 3' proximal to the translation start codon of genes of interest in order for region-specific reverse transcription. Such a region of complementarity can be within the region that is 30 nucleotides upstream (i.e., on the 5' side) and 30 nucleotides downstream (i.e., on the 3' side) of the translation start codon. Alternatively, the region can be within or equal to 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleotides upstream in combination with within or equal to 29, 28, 27, 26, 25, 24, 23, 22, 21, 20, 19, 18, 17, 16, 15, 14, 13, 12, 11, 10, 9, 8, or fewer nucleotides downstream, respectively, of the translation start codon, or any range in between, inclusive, such as 3 nucleotides downstream and 11 nucleotides upstream of the translation start codon. The 3' region sequence of complementarity should also have a melting temperature that is at or above the active temperature of the reverse transcriptase, such as at least about 40° C., 41° C., 42° C., 43° C., 44° C., 45° C., 46° C., 47° C., 48° C., 49° C., or 50° C., or any range in between, inclusive, such as between about 40° C. and 50° C. The 5' portion, alternatively referred to as a 5' region, of primer A has a sequence that is substantially identical to the 3' region of a reverse amplification primer described further below in order to permit nucleic acid amplification. This 5' region should have a melting temperature at or above the active temperature of the DNA polymerase in the nucleic acid amplification process, such as at least about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., or more, or any range in between, inclusive, such as between about 50° C. and 65° C.

In some embodiments, it is contemplated that a BR (reverse amplification primer) binds a few nucleotides, such as 1, 2, 3, 4, 5, 6, 7, or 8, nucleotides downstream of the RNA binding region of the RT primer (i.e., into the region that is formed by reverse transcription reaction), provided the overlap between BF and BR is not too large to cause substantial primer-dimer formation. In such embodiments, the number of nucleotides downstream is minimized due to the small size of the ribosome footprint.

The terms "3' region" and "5' region" with respect to any nucleic acid described herein, such as an oligonucleotide of the present invention, refers to the relative orientation of a particular sequence with respect to the 5' (upstream)-to-3'

(downstream) organization of nucleic acid polymers. Thus, in one embodiment, a 3' region indicates a sequence region that is downstream of another sequence on the same nucleic acid molecule. In another embodiment, a 5' region indicates a sequence region that is upstream of another sequence on the same nucleic acid molecule. In some embodiments, a 3' region or a 5' region can be or comprise a sequence at the very 3' end or 5' end, respectively, of a nucleic acid molecule.

As used herein, the term "active temperature" with respect to an enzyme refers to the temperature at which the enzyme has sufficient activity to mediate its enzymatic function to generate detectable nucleic acid molecules according to the methods of the present invention. For example, commercially available reverse transcriptase enzymes generally have optimal activity sufficient for producing cDNA in quantities that can be detected according to standard laboratory techniques used in the methods according to the present invention at between about 40° C. and 50° C. Many wild-type and recombinant reverse transcriptases are known and the temperature and other conditions for sufficient and/or optimal enzyme activity, processivity, maximum cDNA extension length, and the like, are also well-known and can be paired with oligonucleotides according to the oligonucleotide design parameters described herein and the methods of the present invention (see the World Wide Web at, for example, promega.com/resources/pubhub/choosing-the-right-reverse-transcriptase/and sigmaaldrich.com/technical-documents/articles/biology/reverse-transcription-.html).

An oligonucleotide's thermal melting point (Tm) is the temperature at which about 50% of the oligonucleotide and its complement are in duplex. The Tm of a double stranded region of an oligonucleotide can be calculated from the oligonucleotide sequence using methods that are well-known in the art. For example, the Tm of an oligonucleotide can be calculated using the following formula: Tm=4° C.×(number of G's and C's in the primer)+2° C.×(number of A's and T's in the primer). This formula is valid for oligonucleotides having a double stranded region of <14 bases and assumes that the reaction is carried out in the presence of 50 mM monovalent cations. For longer oligonucleotides having a double stranded region >14 bases, the following formula can be used: Tm=64.9° C.+41° C.×(number of G's and C's in the primer-16.4)/N, where N is the length of the primer. Another commonly used formula takes into account the salt concentration of the reaction (Rychlik and Rhoads (1989) *Nucl. Acids Res.* 17:8543; PCR Core Systems Technical Bulletin #TB254, Promega Corporation; Sambrook, J., Fritsch, E. F. and Maniatis, T. (1989) Molecular Cloning: A Laboratory Manual, Cold Spring Harbor Laboratory Press, Cold Spring Harbor, N.Y. and Mueller, P. R. et al. (1993) In: Current Protocols in Molecular Biology 15.5, Greene Publishing Associates, Inc. and John Wiley and Sons, New York): Tm=81.5° C.+16.6° C.×($\log_{10}$[Na$^+$]+[K$^+$])+0.41° C.×(% GC)-675/N, where N is the number of nucleotides in the oligonucleotide.

The most sophisticated Tm calculations take into account the exact sequence and base stacking parameters, not just the base composition (as described in Borer et al. (1974) *J. Mol. Biol.* 86:843; SantaLucia (1998) *Proc. Nat. Acad. Sci. USA* 95:1460; Allawi and SantaLucia (1997) *Biochem.* 36:10581; and von Ahsen et al. (1999) *Clin. Chem.* 45:2094), as Tm=ΔH kcal ° C.*Mol ΔS+R ln ([primer]/2) −273.15° C., where ΔH is the enthalpy of base stacking interactions adjusted for helix initiation factors, ΔS is the entropy of base stacking adjusted for helix initiation factors and for the contributions of salts to the entropy of the system, and R is the universal gas constant (1.987 Cal/° C. mole). This equation, as implemented above, is valid if i) the primer is not self-complementary, ii) the primer concentration is much greater than the target concentration; iii) the primer is an "oligonucleotide" rather than a long polymer; and iv) the salt effects on polymers is significantly different from those on oligos. For self-complementary oligonucleotides, the denominator of the equation becomes ΔS+R ln([primer]/4). If the concentrations are almost equal, the denominator of the equation becomes ΔS+R ln([primer]−[target]/2).

Numerous electronic and commercially available tools are available on the World Wide Web for calculating the melting temperatures of oligonucleotides (see, for example, the OligoAnalyazer 3.1 calculator available on the Integrated DNA Technologies web site).

An oligonucleotide's annealing temperature is generally about 5° C. below the Tm of the oligonucleotide, although it can be determined to be about 4.9, 4.8, 4.7, 4.6, 4.5, 4.4, 4.3, 4.2, 4.1, 3.9, 3.8, 3.7, 3.6, 3.5, 3.4, 3.3, 3.2, 3.1, 3.0° C., or less, or any range in between, inclusive, such as about 5° C. to about 3° C. below the oligonucleotide's Tm.

In some embodiments, in between the 3' region of primer A and the 5' region of primer A is provided a spacer region to increase the length of the oligonucleotide, such that the total length of the oligonucleotide is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides in length, or any range in between, inclusive, such as between about 50 and about 150 nucleotides in length. The actual length of the reverse transcription primer is less important than that the final nucleic acid amplification (e.g., qPCR) product is of sufficient length for detection, such as using a dye whose fluorescence intensity and/or spectrum changes upon binding to double-stranded DNA like a double-stranded nucleic acid intercalating dye (e.g., SYBR® dyes). It is possible to make up the length by using a longer forward or reverse PCR primer. For example, it is contemplated that a reverse transcription primer can be just the RNA-binding region and that a nucleic acid amplification product length (e.g., qPCR product length) is made sufficiently long by the use of long reverse and/or forward PCR primers and the spacer region would be very short or non-existent.

Nucleic acid amplification oligonucleotides (e.g., primers BF and BR in FIG. 1) are also generally designed according to certain parameters and can have physical attributes according to those described above for reverse transcription oligonucleotides and/or as described below (e.g., similar lengths of oligonucleotides, similar lengths of amplified nucleic acids whether by linear amplification in reverse transcription or exponential amplification such as by qPCR, similar modifications, etc.). For example, primer BF has a sequence that is complementary to a portion or region that is more 3' (i.e., more 5' in RNA coordinates) of the cDNA as compared with the sequence of the corresponding reverse transcription primer. Thus, the 3' portion, alternatively referred to as a 3' region, of primer BF is identical in sequence, while accounting for it being DNA rather than RNA, to a region mostly 5' proximal to the translation initiation site in order to permit region-specific amplification by qPCR. Such a region of complementarity can be within the region that is 30 nucleotides upstream (i.e., on the 5' side) and 30 nucleotides downstream (i.e., on the 3' side) of the translation start codon. Alternatively, the region can be within or equal to 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleotides upstream in combination with within or equal to 0, 1, 2, 3, 4, 5, 6, 7, 8, 9, 10 or fewer nucleotides downstream, respectively, of the translation start codon, or any range in between, inclusive, such as 13 nucleotides upstream and 0 nucleotides upstream of the translation start codon. The relative 5' shift in position of primer BF relative to primer A results in a sufficiently small overlap in order to avoid the formation of unwanted nucleic acid products, such as qPCR primer dimers to an extent that would detrimentally reduce the ability to detect and quantify nucleic acid amplification products of interest. In some embodiments, the overlap in the region targeted by primers A and BF is less than about 0, 1, 2, 3, 4, 5, 6, 7, or 8 nucleotides, or any range in between, such as between 1 and 3 nucleotides. Some portion of primer BR, such as the 3' region of primer BR, is identical to a portion of the 5' region of primer A as described above. The binding regions of primer BF and BR can be designed to have a melting temperature at or above the active temperature of the DNA polymerase in the nucleic acid amplification process, such as at least about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., or more, or any range in between, inclusive, such as between about 50° C. and 65° C. Nucleic acid amplification using the BF and BR primers can result in a nucleic acid amplification product that is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 260, 270, 280, 290, 300, 310, 320, 330, 340, 350, 360, 370, 380, 390, 400, 410, 420, 430, 440, 450, 460, 470, 480, 490, 500, or more nucleotides in length, or any range in between, inclusive, such as between about 20 and about 500 nucleotides in length, between about 50 and about 150 nucleotides in length, etc. For nucleic acid amplification using a dye whose fluorescence intensity and/or spectrum changes upon binding to double-stranded DNA (e.g., intercalating dyes) as detectable labels, such a length of at least about 50 base pairs allows for reliable detection of the label, although shorter oligonucleotides may also work reliably. Amplification oligonucleotides, such as forward and reverse primers, can also be extended on their 5' ends, such as through the incorporation of additional nucleotide sequences sequences, to increase final amplification product length.

The short binding regions in primers A (RNA binding region) and BF, as well as binding regions of BF and BR to cDNA and its complementary strand, respectively, may lead to melting temperatures which may be lower than the manufacturers' recommended optimum reaction temperatures for the reverse transcriptase and qPCR polymerase.

Therefore, in some embodiments, a ramped temperature protocol can be used to balance the effects of primer-template de-annealing and enzyme activity. In one embodiment, for reverse transcription, the temperature can be increased in steps (i.e., ramped) of about 1° C., 2° C., 3° C., 4° C., 5° C., or more at varying time intervals of about every 1 minute, 2 minutes, 3 minutes, 4 minutes, 5 minutes, 6 minutes, 7 minutes, 8 minutes, 9 minutes, 10 minutes, and the like, or any range in between inclusive. For example, a reverse transcription temperature-ramped protocol can have incubation at 40° C., 42° C., 44° C., 46° C., 48° C., and 50° C., in this order, for 10 minutes at each temperature. Similarly, for nucleic acid amplification using PCR, the temperature and time hold thereof can be changed in steps (i.e., ramped) within each amplification cycle in steps of about 1° C., 2° C., 3° C., 4° C., 5° C., or more at varying time intervals of about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more seconds. For example, a nucleic acid amplification method can have a thermocycling protocol of 50° C. for 15 seconds, 55° C. for 15 seconds, 60° C. for 15 seconds, and 65° C. for 45 seconds, in this order, during the annealing and elongation phase, with signal detection at the latter part of the 65° C. step.

In certain embodiments, the regions of complementarity within the oligonucleotides can be at the end of the oligonucleotides, substantially at the end of the oligonucleotides (e.g., the end of the homology region is within about 30%, 25%, 20%, 15%, 10%, 5%, 1% or less of the end of the oligonucleotide), or internal to the oligonucleotide.

As described in the Examples, oligonucleotides can be pooled (e.g., at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 100 or more, or any range in between of reverse transcription primers, such as 2-5 reverse transcription primers and/or at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 100 or more, or any range in between of nucleic acid amplification primer pairs, such as 2-5 pairs of nucleic acid amplification primers, all either alone or in addition to other oligonucleotides, such as 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 100 or more, or any range in between oligonucleotide probes). For example, a mix of reverse transcription primers can be used in the same reaction for multiplex reverse transcription. Similarly, a mix of nucleic acid amplification primer pairs, either alone or in further combination with other oligonucleotides like nucleic acid probes, can be used in the nucleic acid amplification reaction. Moreover, different arrangements of reverse transcription and/or nucleic acid amplification primers can be used if reverse transcription and nucleic acid amplification are to be performed in the same vessel. The number of combinations of oligonucleotides in a reaction can be large and possibly up to reverse transcription and/or detection of all known genes (e.g., the entire translatome).

In addition to the particular considerations for oligonucleotide design useful for the methods of the present invention described above, well-known considerations in the art are also useful in designing the reverse transcription and/or nucleic acid amplification oligonucleotides. For example, the sequences for binding target regions can be chosen such that, where possible, the combined effect of reverse transcription and nucleic acid amplification is to detect abundance of sequences arising only from the gene of interest. All complementary binding regions in reverse transcription and nucleic acid amplification should be of sufficient length for adequate binding of the reverse transcriptase and DNA polymerase enzymes, respectively. Avoiding extreme GC content, hairpin loop structures, dimer formation sequences, and the like can also be used to inform the oligonucleotide design.

A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The term "perfectly complementary" means that all the contiguous residues of a nucleic acid sequence will hydrogen bond with the same number of contiguous residues in a second nucleic acid sequence. The term "substantially complementary" as used herein refers to a degree of complementarity that is at least about 80%, 81%, 82%, 83%, 84%, 85%, 86%, 87%, 88%, 89%, 90%, 91%, 92%, 93%, 94%, 95%, 96%, 97%, 98%, 99%, or greater, such as 100% identity, over a region of at least about 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 20, 125, 130, 135, 140, 145, 150, or more, nucleotides, such as the entire length of a compared nucleic acid sequence, or any range in between, inclusive, such as 13-20 nucleotides, or refers to two nucleic acids that hybridize under stringent conditions. In addition to sequence complementarity, generally, oligonucleotides for use according to the methods of the present invention and having substantial complementarity with a target sequence specifically and predominantly hybridize with the target sequence and substantially (e.g., essentially) do not hybridize to non-target sequences under the methods' conditions. However, due to short hybridization lengths involved in the amplification and detection of target nucleic acids, in certain embodiments, it may not be possible to avoid hybridization to non-target similar sequences. Such embodiments are within the scope of the present invention if the non-target sequences recognized do not significantly distract the investigator from analyzing the target sequences (e.g., the non-target sequences are not highly translated, the non-target sequences are from different genes that yet serve redundant biological functions, etc.).

The term "substantially identical" as used herein refers to a degree of homology that is at least about 80%, 81%, 82%, 83%, 84%, 85%, 86%, 87%, 88%, 89%, 90%, 91%, 92%, 93%, 94%, 95%, 96%, 97%, 98%, 99%, or greater, such as 100% identity, over a region of at least about 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 20, 125, 130, 135, 140, 145, 150, or more, nucleotides, such as the entire length of a compared nucleic acid sequence, or any range in between, inclusive, such as 13-20 nucleotides, between two nucleic acid sequences. In embodiments, where an RNA sequence is compared to a DNA sequence, then uridine nucleotides are considered the same as thymidine nucleotides for purposes of sequence comparison and homology determinations.

In some embodiments, oligonucleotides can comprise one or more modifications, such as chemical modifications at the 3' end, at the 5' end, internally, within a base, within the backbone, and the like, either alone or in combination, in order to provide the oligonucleotide with a new or enhanced characteristic, such as improved stability or resistance to degradation (see U.S. Pat. Publ. 2016/0108470).

For example, in one embodiment, an oligonucleotide is chemically modified at its 3'-end, such as with a dideoxyribonucleotide, to block the oligonucleotide from participating in primer extension. For example, the 3'-terminus of an oligonucleotide may be capped at the 3' terminus with a dideoxythymine triphosphate using a Klenow fragment mutant (F762Y) of DNA polymerase I (*Escherichia coli*) or T7 DNA polymerase (Tabor and Richardson (1995) *Proc. Natl. Acad. Sci. USA* 92:6339-6343).

In another embodiment, the oligonucleotide may have one or more blocking agents. A blocking agent refers to a nucleotide (or derivatives thereof), modified oligonucleotides and/or one or more other modifications which are incorporated into the nucleic acid inhibitors of the invention to prevent or inhibit degradation or digestion of such nucleic acid molecules by DNase activity.

An oligonucleotide can comprise a detectable label. The terms "label," "detectable moiety," "detectable agent," and like terms refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$, and the like), electron-dense reagents, enzymes, biotin, digoxigenin, or haptens and proteins or other entities which can be made detectable, e.g., by affinity. The term "tag" can be used synonymously with the term "label," but generally refers to an affinity-based moiety, e.g., a "His tag" for purification, or a "streptavidin tag" that interacts with biotin.

Any method known in the art for conjugating a nucleic acid or other biomolecule to a label may be employed, e.g., using methods described in Hermanson, Bioconjugate Techniques 1996, Academic Press, Inc., San Diego. For example, labeling can be performed in a non-enzymatic manner. For example, the Universal Labeling System™ (ULS™) technology can be used (ULS™ array CGH Labeling Kit; manufactured by Kreatech Biotechnology BV Company) and the like can be also used. Briefly, ULS™ labeling is based on the stable binding properties of platinum (II) to nucleic acids (van Gijlswijk et al. (2001) *Expert Rev. Mol. Diagn.* 1:81-91). The ULS molecule consists of a monofunctional platinum complex coupled to a detectable molecule of choice. Alternative methods may be used for labeling the RNA, for example, as set out in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). As a method for fluorescent labeling, a direct labeling method or an indirect labeling method may be used. The direct labeling method means a method where a nucleic acid is transformed into a single-strand one, a short-chain nucleic acid is hybridized thereto, and a nucleotide compound to which a fluorescent substance (e.g., Cy-dye) has been bound is mixed with the nucleotide, thereby the nucleic acid is labeled in one step. The indirect labeling method means a method where a nucleic acid is transformed into a single-strand one, a short-chain nucleic acid is hybridized thereto, a nucleotide compound having a substituent capable of being bound to a fluorescent substance (e.g., Cy-dye), for example, a nucleotide compound having an aminoallyl group and the natural nucleotide are mixed together, a nucleic acid having the substituent is first synthesized, and then a fluorescent substance (e.g., Cy-dye) is bound through the aminoallyl group, thereby the nucleic acid being labeled. As methods for introducing a labeling compound such as a fluorescent substance into the nucleic acid, a random primer method (primer extension method), a nick translation method, a PCR method, a terminal labeling method, and the like may be used.

Other labeling methods are also well-known. For example, the random primer method is a method where a random primer nucleic acid having several by (base pair) to over ten by is hybridized and amplification and labeling are simultaneously performed using a polymerase, thereby a labeled nucleic acid being synthesized. The nick translation method is a method where, for example, a double-strand nucleic acid to which nick has been introduced with DNase I is subjected to the action of a DNA polymerase to decompose DNA and simultaneously synthesize a labeled nucleic acid by the polymerase activity. The PCR method is a method where two kinds of primers are prepared and a PCR reaction is carried out using the primers, thereby amplification and labeling being simultaneously performed to obtain a labeled nucleic acid. The terminal labeling method is a method where, in a method of labeling a 5'-end, a labeling compound such as a fluorescent substance is incorporated into a 5'-end of a nucleic acid dephosphorylated with an alkaline phosphatase by a phosphorylation reaction with a T4 polynucleotide kinase. A method of labeling 3'-end is a method where a labeling compound such as a fluorescent substance is added to a 3'-end of a nucleic acid with a terminal transferase. As the labeled sample nucleic acid or the like, it is also possible to use an unpurified solution containing the same. In the case of using such an unpurified solution, an enzyme and the like still remain in the solution and hence, after preparation, it is preferable to deactivate the activity of the enzyme remaining in the solution. It is based on the viewpoint of preventing the influence on reproducibility of data. As methods for deactivating the enzyme, any methods may be possible as long as they can deactivate the enzyme but it is preferable to perform any one or both of a method of adding a chelating agent or a heating treatment at 60° C. or higher. The heating temperature is preferably 60° C. or higher. The heating time is sufficiently 1 minute or more and most preferably, it is preferred to perform the heating treatment at 65° C. or higher for 5 minutes or more. Moreover, in the case of labeling method using a Klenow fragment, it is also possible to deactivate the activity of the enzyme using a vortex mixer or the like.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule. The signal from the label can be indicative of the amount of the labeled molecule.

One type of label is a fluorochrome. As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides energy that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention, including, for example, Alexa Fluor™ 350, Alexa Fluor™ 430, Alexa Fluor™ 488, Alexa Fluor™ 532, Alexa Fluor™ 546, Alexa Fluor™ 568, Alexa Fluor™ 594, Alexa Fluor™ 633, Alexa Fluor™ 647, Alexa Fluor™ 660, Alexa Fluor™ 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY® FL, BODIPY® 630/650, BODIPY® 6501665, BODIPYTMR-X®, BODIPY TR-X®, Dialkylaminocoumarin, Cy5.5, Cy5, Cy3.5, Cy3, DTPA $(Eu^{3+})$-AMCA and TTHA$(Eu^{3+})$AMCA.

In one embodiment, reporter molecules are fluorescent organic dyes derivatized for attachment to the terminal 3' or terminal 5' ends of the probe via a linking moiety.

Preferably, quencher molecules are also organic dyes, which may or may not be fluorescent, depending on the embodiment of the invention. The quencher molecule can be fluorescent. Generally, whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange, N-(p-(2-benzoxazolyl)phenyl)maleimide, benzoxadiazoles, stilbenes, pyrenes, and the like. In one embodiment, reporter and quencher molecules are selected from fluorescein and rhodamine dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like. Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

An oligonucleotide can comprise a nucleic acid affinity tag. As used herein, "affinity tag" can refer to either a peptide affinity tag or a nucleic acid affinity tag. Affinity tag generally refer to a protein or nucleic acid sequence that can be bound to a molecule (e.g., bound by a small molecule, protein, covalent bond). An affinity tag can be a non-native sequence. A peptide affinity tag can comprise a peptide. A peptide affinity tag can be one that is able to be part of a split system (e.g., two inactive peptide fragments can combine together in trans to form an active affinity tag). A nucleic acid affinity tag can comprise a nucleic acid. A nucleic acid affinity tag can be a sequence that can selectively bind to a known nucleic acid sequence (e.g., through hybridization). A nucleic acid affinity tag can be a sequence that can selectively bind to a protein. An affinity tag can be fused to a native protein. An affinity tag can be fused to a nucleotide sequence. Sometimes, one, two, or a plurality of affinity tags can be fused to a native protein or nucleotide sequence. An affinity tag can be introduced into a oligonucleotide using methods of in vitro or in vivo transcription. Nucleic acid affinity tags can include, for example, a chemical tag, an RNA-binding protein binding sequence, a DNA-binding protein binding sequence, a sequence hybridizable to an affinity-tagged polynucleotide, a synthetic RNA aptamer, or a synthetic DNA aptamer. Examples of chemical nucleic acid affinity tags can include, but are not limited to, ribonucleotriphosphates containing biotin, fluorescent dyes, and digoxeginin. Examples of protein-binding nucleic acid affinity tags can include, but are not limited to, the MS2 binding sequence, the U1A binding sequence, stem-loop binding protein sequences, the boxB sequence, the eIF4A sequence, or any sequence recognized by an RNA binding protein. Examples of nucleic acid affinity-tagged oligonucleotides can include, but are not limited to, biotinylated oligonucleotides, 2,4-dinitrophenyl oligonucleotides, fluorescein oligonucleotides, and primary amine-conjugated oligonucleotides.

Oligonucleotides can have a modified nucleoside (i.e., base-sugar combination).

The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within oligonucleotides, the phosphate groups can commonly be referred to as forming the internucleoside backbone of the oligonucleotide. The linkage or backbone of the oligonucleotide can be a 3' to 5' phosphodiester linkage.

An oligonucleotide can comprise a modified backbone and/or modified internucleoside linkages. Modified backbones can include those that retain a phosphorus atom in the backbone and those that do not have a phosphorus atom in the backbone. Suitable modified oligonucleotide backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and amino alkylphosphoramidates, phosphorodiamidates, thionophosphoramidates, thionoalkylphosphonates, thionoalkylphosphotriesters, sclenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable oligonucleotides having inverted polarity can comprise a single 3' to 3' linkage at the 3'-most internucleotide linkage (i.e., a single inverted nucleoside residue in which the nucleobase is missing or has a hydroxyl group in place thereof). Various salts (e.g., potassium chloride or sodium chloride), mixed salts, and free acid forms can also be included. An oligonucleotide can comprise one or more phosphorothioate and/or heteroatom internucleoside linkages, in particular —CH$_2$—NH—O—CH$_2$—, —CH$_2$—N(CH$_3$)—O—CH$_2$— (i.e., a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—).

An oligonucleotide can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

An oligonucleotide can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

An oligonucleotide can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

An oligonucleotide can comprise linked morpholino units (i.e., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of oligonucleotides. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

An oligonucleotide can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. A sugar substituent group can be selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification can include 2'-methoxyethoxy(2'-O—$CH_2CH_2OCH_3$, also known as 2'-O-(2-methoxyethyl) or 2'-MOE (i.e., an alkoxyalkoxy group). A further suitable modification can include 2'-dimethylaminooxyethoxy (i.e., a $O(CH_2)_2ON$ $(CH_3)_2$ group, also known as 2'-DMAOE), and 2'-dimethylaminoethoxyethoxy (also known as 2'-O-dimethyl-aminoethoxy-ethyl or 2'-DMAEOE) (i.e., 2'-O—$CH_2O$—$CH_2$—$N(CH_3)$ 2).

Other suitable sugar substituent groups can include methoxy (—O—$CH_3$), aminopropoxy (—$OCH_2CH_2CH_2NH_2$), allyl (—$CH_2$—CH(=$CH_2$)), —O-allyl (—O—$CH_2$—CH(=$CH_2$)) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A oligonucleotide may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C(=C—$CH_3$)) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b)(1,4)benzoxazin-2(3H)-one), carbazole cytidine (2H-pyrimido(4,5-b)indol-2-one), pyridoindole cytidine (Hpyrido(3',2':4,5)pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions can increase nucleic acid duplex stability by 0.6-1.2.degree. C. and can be suitable base substitutions (e.g., when combined with 2'-O-methoxyethyl sugar modifications).

A modification of an oligonucleotide can comprise chemically linking to the oligonucleotide one or more moieties or conjugates that can enhance the activity, cellular distribution or cellular uptake of the oligonucleotide. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid, a thioether (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

In some embodiments, the nucleic acid amplification oligonucleotides are used in a real-time nucleic acid amplification method. Since post-amplification amplicon detection is both laborious and time consuming, real-time methods have been developed to monitor amplification during the amplification and are well-known in the art. These methods typically employ fluorescently labeled probes that bind to the newly synthesized DNA or dyes whose fluorescence emission is increased when intercalated into double stranded DNA. Real-time detection methodologies are applicable to PCR detection of target nucleic acid sequences in genomic DNA or genomic RNA.

Quantitative PCR (qPCR) is used to amplify and simultaneously quantify one or more targeted nucleic acid templates. The quantity can be either an absolute number of copies or a relative amount when normalized to a known DNA input (e.g., an internal or external control) or additional normalizing genes (e.g., housekeeping gene such as beta-actin). Three common methods for qPCR detection are: (1) non-specific fluorescent dyes that intercalate with double-stranded DNA, (2) sequence-specific probe(s) labeled with a fluorescent reporter which permits detection only after hybridization of the probe (e.g., molecular beacon), and (3) sequence-specific probes that are hydrolyzed by a PCR polymerase, such as TaqMan® probes. qPCR is compatible both with quantitative competitive PCR, where internal competitor for each target sequence is used for normalization, and with quantitative comparative PCR using a normalization gene contained within the sample, or a housekeeping gene for RT-PCR (see Held et al. (1996) *Genome Research* 6:986-994).

The probes are generally designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM, TAMRA, VIC, JOE, Cy3, Cy5, and Texas Red.) Acceptor chromophores are chosen so that their excitation spectra overlap with the emission spectrum of the donor. An example of such a pair is FAM-TAMRA. There are also non fluorescent acceptors that will quench a wide range of donors. Other examples of appropriate donor-acceptor FRET pairs will be known to those skilled in the art. Common examples of FRET probes that can be used for real-time detection of PCR include molecular beacons (e.g., U.S. Pat. No. 5,925,517), TaqMan™ probes (e.g., U.S. Pat. Nos. 5,210,015 and 5,487,972), and CataCleave™ probes (e.g., U.S. Pat. No. 5,763,181).

Nucleic acid amplification can be performed using well-known and commercially available instruments. For example, a qPCR reaction can be performed using an Applied Biosystems® 7300 Real Time PCR System, which was used in the examples described below. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

In some embodiments, detected nucleic acid amplification product amounts of interest are compared with such amounts of a reference nucleic acid amplification product. For example, a reference can be another experimental gene of interest or a control that is expected to stay constant in the sample. For the reference, a housekeeping gene (e.g., a gene that is required for the maintenance of basic cellular function) can be used that is expected to stay constant in a sample. A housekeeping gene that can be used as reference in the methods described herein can include a gene that encodes a transcription factor, a transcription repressor, an RNA splicing gene, a translation factor, tRNA synthetase, RNA binding protein, ribosomal protein, RNA polymerase, protein processing protein, heat shock protein, histone, cell cycle regulator, apoptosis regulator, oncogene, DNA repair/replication gene, carbohydrate metabolism regulator, citric acid cycle regulator, lipid metabolism regulator, amino acid metabolism regulator, nucleotide synthesis regulator, NADH dehydrogenase, cytochrome C oxidase, ATPase, mitochondrial protein, lysosomal protein, proteosomal protein, ribonuclease, oxidase/reductase, cytoskeletal protein, cell adhesion protein, channel or transporter, receptor, kinase, growth factor, tissue necrosis factor, etc.

Specific examples of housekeeping genes that can be used in the methods described include, e.g., HSP90, ACTB, UBC and TUBA1B. In some embodiments, the entire translatome is globally decreased or increased such that the term "housekeeping gene" refers to a gene whose trend in change is broadly representative of the majority of the translatome change.

In addition to relative quantitation, the methods of the present invention can incorporate comparisons of the amounts of target nucleic acids in an absolute quantitation mode, such as by comparing the amounts of target nucleic acids fixed standards either in separate reactions or added artificially to the sample in earlier steps.

As described above, one advantage of the methods of the present invention is that size selection is not required. The following mathematical model for RNA degradation demonstrates why the fold-change in measured RNA translation rate is independent of fragment size selection such that size selection is unnecessary according to the methods of the present invention.

Suppose a given gene has T transcripts, which are subjected to degradation as described above. Suppose that under condition C, proportion $r_C$ of transcripts are protected at a pre-defined region by ribosomes of footprint size f and that there is probability p of degradation at any given unprotected nucleotide, then the total number of fragments preserving the entire pre-defined region, i.e. those detectable by qPCR, is $$T \cdot \{r_C + (1-r_C)(1-p)^f\}$$

Suppose that the sample is subjected to size selection preserving all fragments of size f+U or less, where U is a defined nucleotide length, then the number of detectable fragments after size selection $n_C$ is $$n_C = T \cdot \{r_C + (1-r_C)(1-p)^f\} \cdot \{p^2 + 2(1-p)p^2 + 3(1-p)^2 p^2 + \ldots + (U+1)(1-p)^U p^2\}$$

$$n_C = T \cdot \{r_C + (1-r_C)(1-p)^f\} \cdot \{1 - (1-p)^{U+1}(1+p+pU)\}$$

For two conditions C=1 and C=2, the relative fold-change in translation between the conditions is $$\frac{n_1}{n_2} = \frac{T \cdot \{r_1 + (1-r_1)(1-p)^f\} \cdot \{1 - (1-p)^{U+1}(1+p+pU)\}}{T \cdot \{r_2 + (1-r_2)(1-p)^f\} \cdot \{1 - (1-p)^{U+1}(1+p+pU)\}}$$

-continued $$\frac{n_1}{n_2} = \frac{r_1 + (1-r_1)(1-p)^f}{r_2 + (1-r_2)(1-p)^f}$$

Thus, the fold-change in measured translation rate according to the methods of the present invention is independent of the fragment size selected.

In addition to not requiring nucleic acid size selection, the methods of the present invention do not require nucleic acid sequencing or creation and/or analysis of a library formed from generated cDNA. Nevertheless, such methods and additional methods can be performed, if desired. For example, many nucleic acid hybridization-based, sequencing-based, and/or amplification-based assays for detecting and analyzing nucleic acids, such as Southern blotting, Northern blotting, comparative genomic hybridization (CGH), chromosomal microarray analysis (CMA), expression profiling, DNA microarray, high-density oligonucleotide microarray, whole-genome RNA expression array, digital PCR (dPCR), reverse transcription PCR, ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA) (for circularized fragments), invasive cleavage assays, nCounter Analysis (Nanostring technology), genome sequencing, de novo sequencing, pyrosequencing, polony sequencing, copy number variation (CNV) analysis sequencing, small nucleotide polymorphism (SNP) analysis, whole exome sequencing, in situ hybridization, either DNA or RNA fluorescent in situ hybridization (FISH), chromogenic in-situ hybridization (CISH), RNA sequencing, and epigenetic profiling, such as methylation pattern sequencing, phosphorylation pattern sequencing, and the like, can be used.

So-called "next-generation" sequencing techniques that may be amenable to performing large numbers of sequencing reactions in parallel can be performed. Such techniques include pyrosequencing, nanopore sequencing, single base extension using reversible terminators, ligation-based sequencing, single molecule sequencing techniques, massively parallel signature sequencing (MPSS) and the like, as described in, for example, U.S. Pat. Nos. 7,057,056; 5,763,594; 6,613,513; 6,841,128; and 6,828,100; and PCT Published Application Nos. WO 07/121,489 A2 and WO 06/084132 A2.

Many technologies using or detecting nucleic acids can also be adapted for arrays, which are sensitive to size variations because a multitude of individual reactions occur in densely packed locations. As used herein, an "array," includes any one-dimensional, two-dimensional or substantially two-dimensional (as well as a three-dimensional) arrangement of addressable regions (i.e., features, e.g., in the form of spots) bearing nucleic acids, particularly oligonucleotides or synthetic mimetics thereof (i.e., the oligonucleotides defined above), and the like. Where the arrays are arrays of nucleic acids, the nucleic acids may be adsorbed, physisorbed, chemisorbed, or covalently attached to the arrays at any point or points along the nucleic acid chain. Array-based assays are well-known in the art and include, for example, comparative genomic hybridization (CGH) and array-based comparative genomic hybridization (aCGH).

C. Kits

The disclosure herein also provides for a kit format which comprises a package unit having one or more reagents for the generation of ribosome-protected nucleic acid fragments and/or amplification of cDNA derived thereof as described herein. The kit may also contain one or more of the following items: buffers, instructions, and positive or negative controls. Kits may include containers of reagents mixed together in suitable proportions for performing the methods described herein. Reagent containers preferably contain reagents in unit quantities that obviate measuring steps when performing the subject methods.

Kits may also contain reagents for quantitative real-time PCR including, but not limited to, a thermostable nucleic acid polymerase, buffers, fluorescent detection reagents, and nucleic acid amplification primers to amplify the real-time PCR products of interest and to allow for the quantitative detection of the target nucleic acid sequence according to the methodology described herein.

In another embodiment, the kit reagents further comprised reagents for the extraction of RNA-ribosome complexes, such as those from a biological sample. Kit reagents may also include reagents for reverse transcription-PCR analysis where applicable.

EXEMPLIFICATION

This invention is further illustrated by the following examples, which should not be construed as limiting.

Example 1: An Embodiment of a Method for Rapid and Targeted Measurement of mRNA Translation Rates Existing commonly used methods for measuring mRNA translation rates, such as polysome profiling and ribosome profiling, are expensive, lengthy, and labor intensive to perform. It has been determined and described herein that alternative methods described herein can overcome such problems to effectively measure mRNA translation rates. Such methods are referred to herein as "Targeted Profiling of Translation Rate" (TPTR) methods. Variations of these methods, such as modifications to protocols, reagents, incubation lengths, and the like, are also contemplated as described herein.

For example, in some embodiments, vacuum aspiration was used to remove media from adherent mammalian cells cultured on plastic surface under suitable conditions. For example, MDA-MB-468 (ATCC, cultured in RPMI media (Gibco) supplemented with 10% fetal bovine serum (Gemini Bioproducts), 1× GlutaMAX (Gibco), 10 mM HEPES (Gibco), 1× Antibiotic-Antimycotic (Gibco)) were cultured in a humidified chamber at 370 and 5% $CO_2$, and were seeded at 500,000 cells in 4 ml media per 9.6 $cm^2$ well (Falcon 6-well tissue-culture treated plate) one day before treatment and subjected to treatment the following day. A cell lysate was then obtained by adding ice-cold PBS supplemented with 100 ug/ml cycloheximide, keeping the PBS/cycloheximide solution in contact with the cells for approximately 15 seconds, and then vacuum aspirating off the PBS/cycloheximide solution, followed by contact with a lysis buffer having 20 mM Tris (pH 7.4), 150 mM NaCl, 5 mM $MgCl_2$, 1 mM DTT, 1 mg/ml cycloheximide, 1% v/v Triton™ X-100, 25 Kunitz units/ml DNase I, at 300 ul per 100 mm cell culture dish or its volume-to-area equivalent. The lysis buffer was mechanically dispersed over the surface of the dish and the dish was transferred to liquid nitrogen in order to freeze the contents. The dish was then transferred onto wet ice and incubated until the contents were thawed. The cells were then mechanically removed from the dish surface using a cell scraper. The removed dish contents were transferred to microcentrifuge tubes on ice and triturated through a 25 gauge needle 10 times. After incubation for approximately 2 to 5 minutes on ice, the triturated dish contents were centrifuged at 20,000×g for 3 to 5 minutes at 4° C. The supernatant was recovered as a clarified lysate and a suitable volume of clarified lysate (e.g., 100 ul) was obtained for processing.

RNase I (1,000 U) was added in a 10 ul volume to every 100 ul of lysate and the mixture was incubated for 1 hour at 4° C. with gentle agitation. RNA fragments were then isolated and purified. Specifically, 440 ul of TRIzol® was added per 110 ul of reaction sample described above. The mixture was mixed and allowed to incubate for 5 minutes at room temperature. Then, 88 ul of chloroform was added per 440 ul of the TRIzol mixture and the resulting mixture was mixed followed by incubation for about 3 minutes at room temperature. The incubated mixture was then centrifuged at 12,000×g for 15 minutes at 4° C. and 250 ul of the upper aqueous phase was recovered. Two ul of GlycoBlue® was added to the recovered upper aqueous phase, the mixture was mixed, 375 ul of 100% isopropanol was added to the mixture, and the resulting mixture was also mixed and allowed to incubate for 30 minutes or longer on dry ice or at a lower temperature. The mixture was then transferred to room temperature to thaw and subsequently centrifuged at 20,000×g for 30 minutes at 4° C. The supernatant was then removed, 1,000 ul of 70% ice-cold ethanol was added, the pellet was washed by mixing, the washed mixture was then centrifuged at 20,000×g for 10 minutes at 4° C., the supernatant was removed, the mixture was incubated at room temperature until the pellet was dry, and the dried pellet was resuspended in 10 ul of water. If the RNA was insufficiently pure, the purification process described could be performed after adding water to 180 ul, 1 ul of GlycoBlue, 20 ul of 3 M NaOAc, mixing, adding 300 ul of 100% isopropanol, and mixing.

The RNA fragments were then reverse transcribed. In particular, 2 ul of primer mix A described below was added to 10 ul of RNA solution and the mixture was incubated for 2 minutes at 80° C. followed by a gradual decrease of 0.3° C. per second until reaching a temperature of 30° C. and then followed by cooling to 4° C. The following components were then added to the recited final concentrations: 1× SuperScript® III first strand buffer, dNTPs at 500 uM each, 5 mM DTT, 20 U SUPERase-IN®, and 200 U SuperScript® III reverse transcriptase. The mixture was incubated using a temperature ramp of 40° C., 42° C., 44° C., 46° C., 48° C., and 50° C. in this order for 10 minutes at each temperature, followed by (a) incubation at 70° C. for 15 minutes and then cooling to 4° C. if cDNA purification is not required, or (b) cooling to 4° C. if cDNA purification is required. If desired, the cDNA is then isolated and purified by adding 2.2 ul of 1 N NaOH per 20 ul of reverse transcription reaction, mixed, incubated for 20 minutes at 98° C., followed by cooling to 4° C., and processed as described above regarding the addition of water to 180 ul, 20 ul of 3 M NaOAc, 2 ul of GlycoBlue, mixing, the addition of 300 ul of 100% isopropanol, mixing, and the following of the additional steps described above.

Quantification of particular cDNA species was then performed using qPCR. Specifically, the cDNA solution was diluted into water to a final volume of 600 ul. The diluted cDNA was then transferred to individual qPCR reactions at 6 ul per reaction into a pre-mixed mixture of 10 ul of 2× SYBR®-Select master mix and 4 ul of primer mix B (described below) and the resulting mixture was mixed. The qPCR reaction was then performed in an Applied Biosystems® 7300 Real Time PCR System with the following protocol: 95° C. for 120 seconds and 40 cycles of [95° C. for 15 seconds, 50° C. for 15 seconds, 55° C. for 15 seconds, 60° C. for 15 seconds, and 65° C. for 45 seconds (a temperature ramp)], wherein the qPCR fluorescence signals were detected at the final step of each cycle.

Finally, the qPCR fluorescence signals were analyzed to calculate abundance of cDNA fragments of interest relative to the abundance of equivalent fragments originating from a reference gene(s).

As described above, primers (e.g., DNA oligonucleotides) are used for reverse transcription and qPCR. The design of the primers was unexpectedly determined to satisfy several criteria for suitability in amplifying and quantitating the abundance of RNA fragments containing a target of interest (e.g., the translation initiation site) from specific genes of interest (FIG. 2). The general primer design principles are described above and in FIG. 2. The specific primer sequences used to measure mRNA translation rates of five genes of mammalian cell line MDA-MB-468 treated with the mTOR inhibitor, Torin-1, for 1 hour, relative to a reference gene, are shown in Table 1 below.

TABLE 1

Primer Sequences

| Target gene | | Primer name and sequence (5' to 3') |
|---|---|---|
| EEF1A1 | A1 | AGCGGATAACAATTTCACACAGGCAGGAAACA GCTATGACAGTCTTTTCCTTTCCC |
| | BF1 | CCCCTAAAAGCCAAAATGGG |
| RPL10 (all isoforms) | A2 | AGCGGATAACAATTTCACACAGGCAGGAAACA GCTATGACGGGCGGCGG |
| | BF2 | GATCCTGGTGTCGCCAT |
| EIF4B (all isoforms) | A3 | AGCGGATAACAATTTCACACAGGCAGGAAACA GCTATGACTTTGCTGAGGCCG |
| | BF3 | TTTCCCTCTCCCAACATGG |
| EIF4E (isoforms 1 & 2) | A4 | AGCGGATAACAATTTCACACAGGCAGGAAACA GCTATGACCGGTTCGACAGTC |
| | BF4 | TCAGATCGATCTAAGATGGCGA |
| ACTB | A5 | AGCGGATAACAATTTCACACAGGCAGGAAACA GCTATGACGGCGATATCATCATC |
| | BF5 | CGCCAGCTCACCATGGA |
| UBC | A6 | AGCGGATAACAATTTCACACAGGCAGGAAACA GCTATGACCTTCACGAAGATCTG |
| | BF6 | GATCGTCACTTGACAATGCAG |
| Common | BR | AGCGGATAACAATTTCACACAGG |

Figure 3:
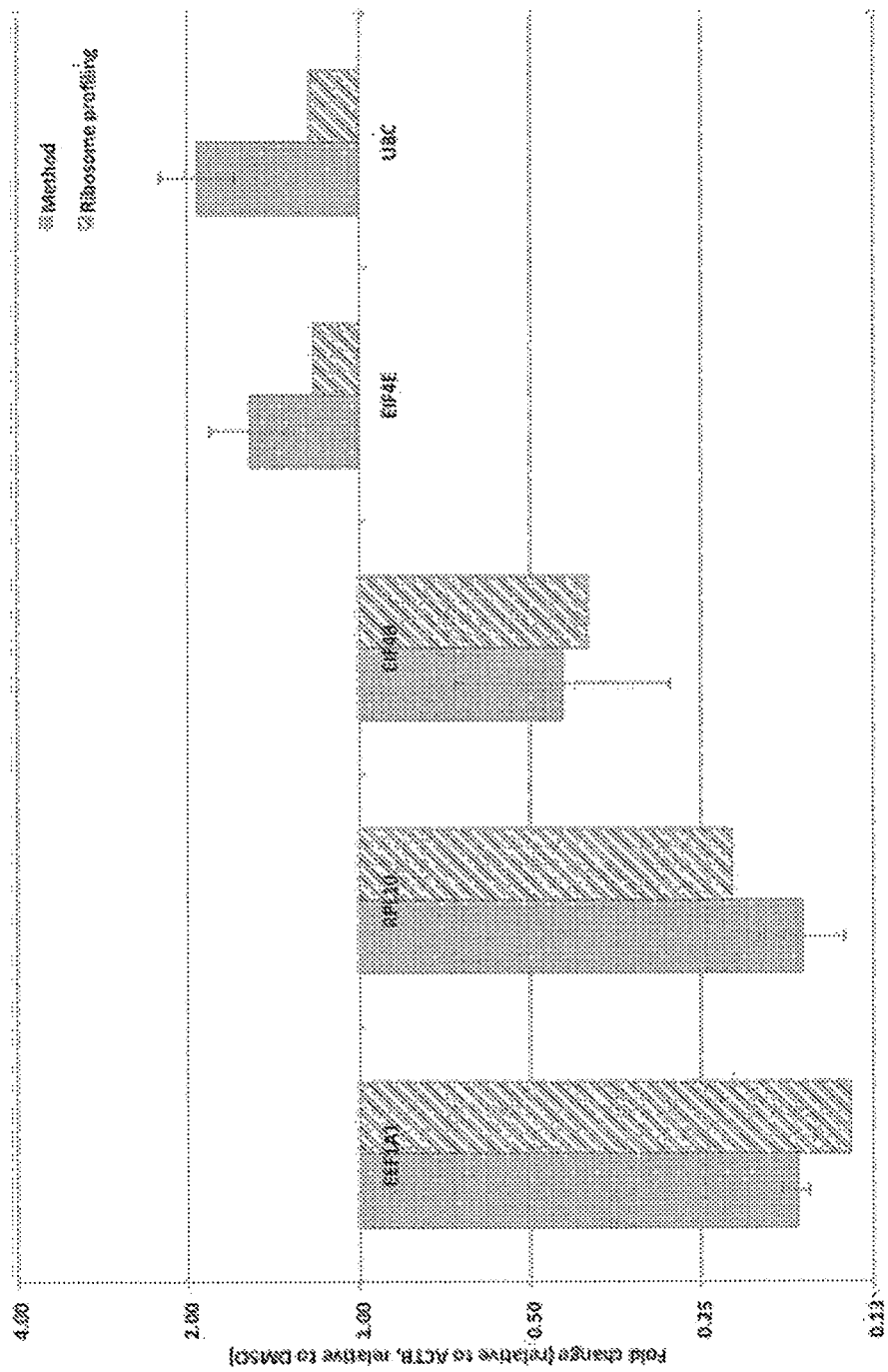
FIG. 3 shows the results of mRNA translation variation of 5 genes of interest relative to β-actin (ACTB) in MDA-MB-468 cells treated with the mTOR inhibitor, Torin-1, for one hour, as determined by ribosome profiling methods of the present invention.

Primer mix A contained a mixture of all of primers A1 to A6 at 1 uM each in water. Primer mix B contained a mixture of two primers, wherein each primer was present at 1 uM in water, one primer was a primer selected from BF1 to BF6 depending upon the target gene of interest, and the second primer was common primer BR. The results of the change in translation rates determined for each of the genes relative to a reference was comparable between the method of the present invention and that of ribosome profiling, which is an established method for determining mRNA translation rates (FIG. 3).

Example 2: Additional Embodiments of Methods for Rapid and Targeted Measurement of mRNA Translation Rates As described above, existing commonly used methods for measuring mRNA translation rates, such as polysome profiling and ribosome profiling, are expensive, lengthy, and labor intensive to perform. It has been determined and described herein that alternative methods described herein can overcome such problems to effectively measure mRNA translation rates. As described above, such methods are referred to herein as "Targeted Profiling of Translation Rate" (TPTR) methods. Variations of these methods, such as modifications to protocols, reagents, incubation lengths, and the like, are also contemplated as described herein.

For example, in some embodiments, vacuum aspiration was used to remove media from adherent mammalian cells cultured on plastic surface under suitable conditions. For example, MDA-MB-468 (ATCC, cultured in RPMI media (Gibco) supplemented with 10% fetal bovine serum (Gemini Bioproducts), 1× GlutaMAX (Gibco), 10 mM HEPES (Gibco), 1× Antibiotic-Antimycotic (Gibco)) and HMECs-hTERT (Clontech, cultured in DMEM/F12 (Gibco) supplemented with 0.6% fetal bovin serum (Gemini Bioproducts), 1 ng/ml cholera toxin (Sigma-Aldrich), 10 ng/ml EGF (Sigma-Aldrich), 10 ug/ml insulin (Gibco), 0.5 ug/ml hydrocortisone (Sigma-Aldrich), 1× Antibiotic-Antimycotic (Gibco)) were cultured in a humidified chamber at 370 and 5% $CO_2$, and were seeded at 500,000 cells in 4 ml media per 9.6 $cm^2$ well (Falcon 6-well tissue-culture treated plate) one day before treatment and subjected to treatment the following day. A cell lysate was then obtained by adding ice-cold PBS supplemented with 100 ug/ml cycloheximide, keeping the PBS/cycloheximide solution in contact with the cells for approximately 60 seconds, and then vacuum aspirating off the PBS/cycloheximide solution, followed by contact with a lysis buffer having 20 mM Tris (pH 7.4), 150 mM NaCl, 5 mM $MgCl_2$, 1 mM DTT, 1 mg/ml cycloheximide, 1% v/v Triton™ X-100, at 200 ul per 9.6 $cm^2$ cell culture area or its volume-to-area equivalent. The lysis buffer was mechanically dispersed over the surface of the dish and the dish was transferred to liquid nitrogen in order to freeze the contents. The dish was then transferred onto wet ice and incubated until the contents were thawed. The cells were then mechanically removed from the dish surface using a cell scraper. The removed dish contents were transferred to microcentrifuge tubes on ice and transferred to liquid nitrogen to freeze the contents. The dish was then transferred onto wet ice and incubated until the contents were thawed, and then centrifuged at 20,000×g for 5 minutes at 4° C. The supernatant was recovered as a clarified lysate, the RNA concentration measured using Qubit® RNA HS assay kit, and a suitable amount of clarified lysate diluted into a suitable volume of lysis buffer (e.g., 500 ng of RNA in 100 ul total volume) was obtained for processing.

RNase I (1,000 U) in a 10 ul volume, and TurboDNase (10 U) in a 5 ul volume, were added to every 100 ul of diluted lysate and the mixture was incubated for 1 hour at 4° C. with gentle agitation. RNA fragments were then isolated and purified. Specifically, 460 ul of TRIzol® was added per 115 ul of reaction sample described above. The mixture was mixed and allowed to incubate for 5 minutes at room temperature. Then, 92 ul of chloroform was added per 460 ul of the TRIzol mixture and the resulting mixture was mixed followed by incubation for about 3 minutes at room temperature. The incubated mixture was then centrifuged at 12,000×g for 15 minutes at 4° C. and 250 ul of the upper aqueous phase was recovered. Two ul of GlycoBlue® (15 mg/ml) was added to the recovered upper aqueous phase, the mixture was mixed, 375 ul of 100% isopropanol was added to the mixture, and the resulting mixture was also mixed and allowed to incubate for 30 minutes or longer on dry ice or at a lower temperature. The mixture was then transferred to room temperature to thaw and subsequently centrifuged at 20,000×g for 30 minutes at 4° C. The supernatant was then removed, 1,000 ul of 70% ice-cold ethanol was added, the pellet was washed by mixing, the washed mixture was then centrifuged at 20,000×g for 10 minutes at 4° C., the supernatant was removed, the mixture was incubated at room temperature until the pellet was dry, and the dried pellet was resuspended in 10 ul of water. If the RNA was insufficiently pure, the purification process described could be performed after adding water to 180 ul, 1 ul of GlycoBlue, 20 ul of 3 M NaOAc, mixing, adding 300 ul of 100% isopropanol, and mixing. This step was not necessary and not done to generate the data described in the figures.

The RNA fragments were then reverse transcribed. In particular, 2 ul of primer mix A described below was added to 10 ul of RNA solution and the mixture was incubated for 2 minutes at 80° C. followed by a gradual decrease of 0.3° C. per second until reaching a temperature of 30° C. and then followed by cooling to 4° C. The following components were then added to the recited final concentrations: 1× SuperScript® III first strand buffer, dNTPs at 500 uM each, 5 mM DTT, 20 U SUPERase-IN®, and 200 U SuperScript® III reverse transcriptase. The mixture was incubated using a temperature ramp of 40° C., 42° C., 44° C., 46° C., 48° C., and 50° C. in this order for 10 minutes at each temperature, followed by (a) incubation at 70° C. for 15 minutes and then cooling to 4° C. if cDNA purification is not required, or (b) cooling to 4° C. if cDNA purification is required. If desired, the cDNA is then isolated and purified by adding 2.2 ul of 1 N NaOH per 20 ul of reverse transcription reaction, mixed, incubated for 20 minutes at 98° C., followed by cooling to 4° C., and processed as described above regarding the addition of water to 178 ul, 20 ul of 3 M NaOAc, 2 ul of GlycoBlue, mixing, the addition of 300 ul of 100% isopropanol, mixing, and the following of the additional steps described above. For the experiments performed to generate the data shown in the figures, option (b) was used.

Quantification of particular cDNA species was then performed using qPCR. Specifically, the cDNA solution was diluted into water to a final volume of 500 ul. The diluted cDNA was then transferred to individual qPCR reactions at 5 ul per reaction into a pre-mixed mixture of 10 ul of 2× SYBR®-Select master mix, 4 ul of primer mix B (described below) and 1 ul of water, and the resulting mixture was mixed. The qPCR reaction was then performed in an Applied Biosystems® 7300 Real Time PCR System with the following protocol: 95° C. for 120 seconds and 40 cycles of [95° C. for 15 seconds, 50° C. for 15 seconds, 55° C. for 15 seconds, 60° C. for 15 seconds, and 65° C. for 45 seconds (a temperature ramp)], wherein the qPCR fluorescence signals were detected at the final step of each cycle, followed by a standard dissociation curve with the following protocol: 95° C. for 15 seconds, 60° C. for 60 seconds, incremental increases in temperature with fluorescence measured at each increment up to 95° C., 95° C. for 15 seconds and 60° C. for 15 seconds.

Finally, the qPCR fluorescence signals were analyzed to calculate abundance of cDNA fragments of interest relative to the abundance of equivalent fragments originating from a reference gene(s), and the dissociation curve data was analyzed to determine the number of distinct qPCR products formed.

As described above, the design of the primers (e.g., DNA oligonucleotides) used for reverse transcription and qPCR were unexpectedly determined to satisfy several criteria for suitability in amplifying and quantitating the abundance of RNA fragments containing a target of interest (e.g., the translation initiation site) from specific genes of interest (FIG. 2). The specific primer sequences used to measure mRNA translation rates of numerous genes of mammalian cell line MDA-MB-468 treated with the mTOR inhibitor, Torin-1, for 1 hour, relative to a reference gene, are shown in Table 2 below.

TABLE 2

Primer Sequences

| Target gene | Primer name and sequence (5' to 3') | |
|---|---|---|
| RPS3A | A1 | AGCGGATAACAATTTCACACAGGAAA CAGCTATGACGTTCTTGCCAACCG |
| | BF1 | TCTCTGACCAGCACCATGG |
| RPS25 | A2 | AGCGGATAACAATTTCACACAGGAAA CAGCTATGACTCGTCCTTAGGCG |
| | BF2 | TCTCCGAGCTTCGCAATGC |
| RPS27 | A3 | AGCGGATAACAATTTCACACAGGAAA CAGCTATGACATCCTTTGCGAGAGG |
| | BF3 | TACGCACACGAGAACATGCC |
| RPL7A | A4 | AGCGGATAACAATTTCACACAGGAAA CAGCTATGACCTTCTTTCCTTTCGGC |
| | BF4 | CCCGCCGCCCAAGAT |
| RPL21 | A5 | AGCGGATAACAATTTCACACAGGAAA CAGCTATGACTCCCTTTGTGTTCG |
| | BF5 | CAGTAATTCGCCAAAATGACGAA |
| EEF1A1 | A6 | AGCGGATAACAATTTCACACAGGAAA CAGCTATGACAGTCTTTTCCTTTCCC |
| | BF6 | CCCCTAAAAGCCAAAATGGG |
| GAPDH | A7 | AGCGGATAACAATTTCACACAGGAAA CAGCTATGACGACCTTCACCTTCC |
| | BF7 | CATCGCTCAGACACCATGG |
| HSPA8 | A8 | AGCGGATAACAATTTCACACAGGAAA CAGCTATGACAGGTCCCTTGGAC |
| | BF8 | TACACCCCAGCAACCATGT |
| TPT1 | A9 | AGCGGATAACAATTTCACACAGGAAA CAGCTATGACGTCCCGGTAGATAATC |
| | BF9 | CCTTCAGTCGCCATCATGAT |
| ATP5F1 | A10 | AGCGGATAACAATTTCACACAGGAAA CAGCTATGACCCACCCGGGACA |
| | BF10 | GGACTTTCGTTGACCATGCTG |
| H3F3A | A11 | AGCGGATAACAATTTCACACAGGAAA CAGCTATGACCTGCTTTGTACGAGC |
| | BF11 | GGAGGTCTCTGTACCATGGC |
| KRT5 | A12 | AGCGGATAACAATTTCACACAGGAAA CAGCTATGACACTTGACTGGCGAG |
| | BF12 | CAGGAACAAGCCACCATGT |
| NDUFC2 | A13 | AGCGGATAACAATTTCACACAGGAAA CAGCTATGACCGCCGTGCGAT |
| | BF13 | GGAAACGGCGTCACCAT |

TABLE 2-continued

Primer Sequences

| Target gene | Primer name and sequence (5' to 3') | |
|---|---|---|
| PPIA | A14 | AGCGGATAACAATTTCACACAGGAAA CAGCTATGACCGGTGGGGTTGA |
| | BF14 | CGTGTACTATTAGCCATGGTCA |
| TUBA1B | A15 | AGCGGATAACAATTTCACACAGGAAA CAGCTATGACGAGATGCACTCACG |
| | BF15 | TAATCCCTAGCCACTATGCGT |
| VAPA | A16 | AGCGGATAACAATTTCACACAGGAAA CAGCTATGACCTGAGGCGGACG |
| | BF16 | CGCTGTCTCTCCGATGGC |
| YWHAQ | A17 | AGCGGATAACAATTTCACACAGGAAA CAGCTATGACCAGCTCAGTCTTCTC |
| | BF17 | GCGCCCGCCATGG |
| ACTB | A18 | AGCGGATAACAATTTCACACAGGAAA CAGCTATGACGGCGATATCATCATC |
| | BF18 | CGCCAGCTCACCATGGA |
| Common | BR | AGCGGATAACAATTTCACACAGG |

Figure 4:
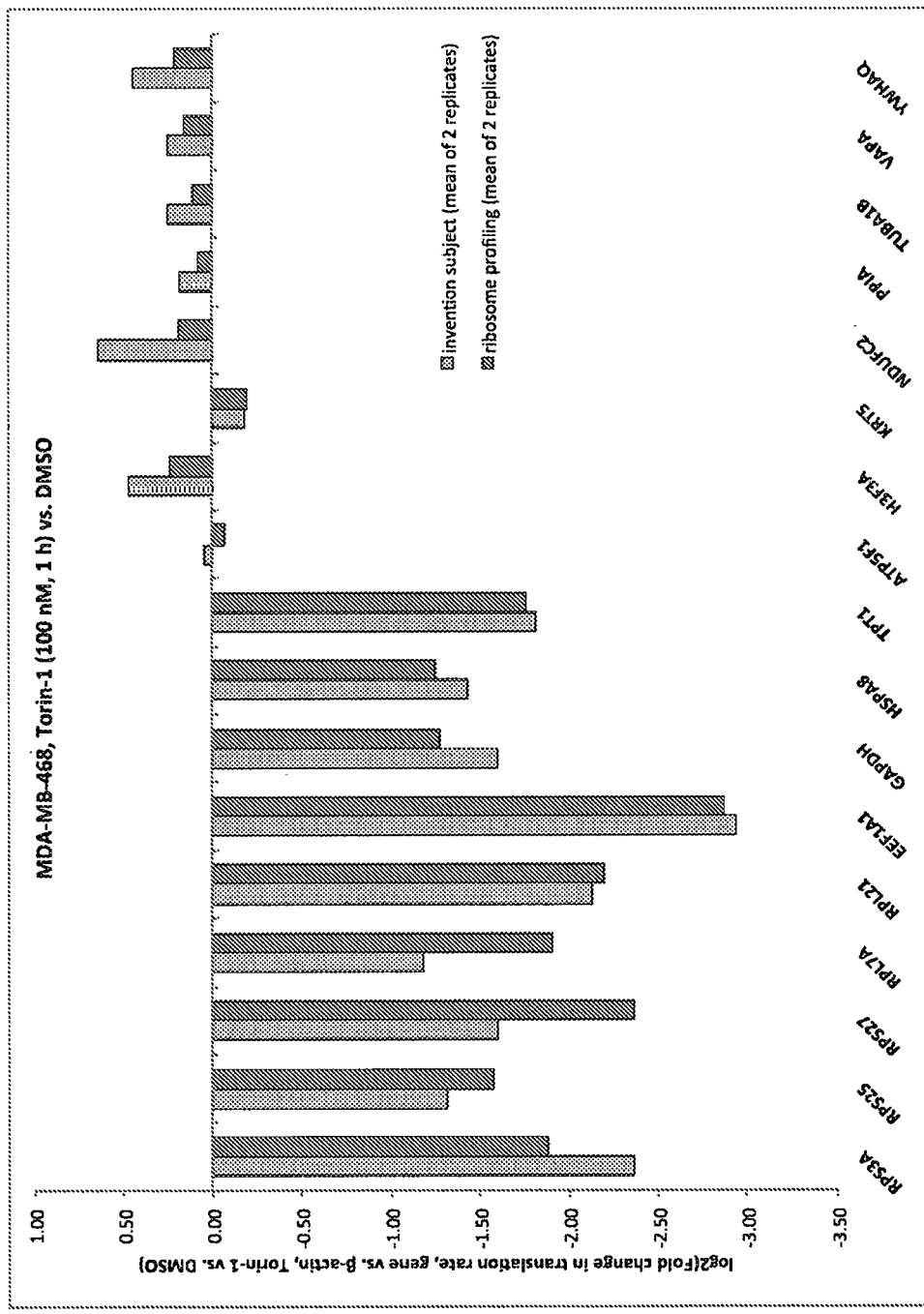
FIG. 4 shows the results of mRNA translation variation of additional representative genes of interest relative to β-actin (ACTB) in MDA-MB-468 cells treated with the mTOR inhibitor, Torin-1, for one hour, as determined by ribosome profiling methods of the present invention.
Figure 5:
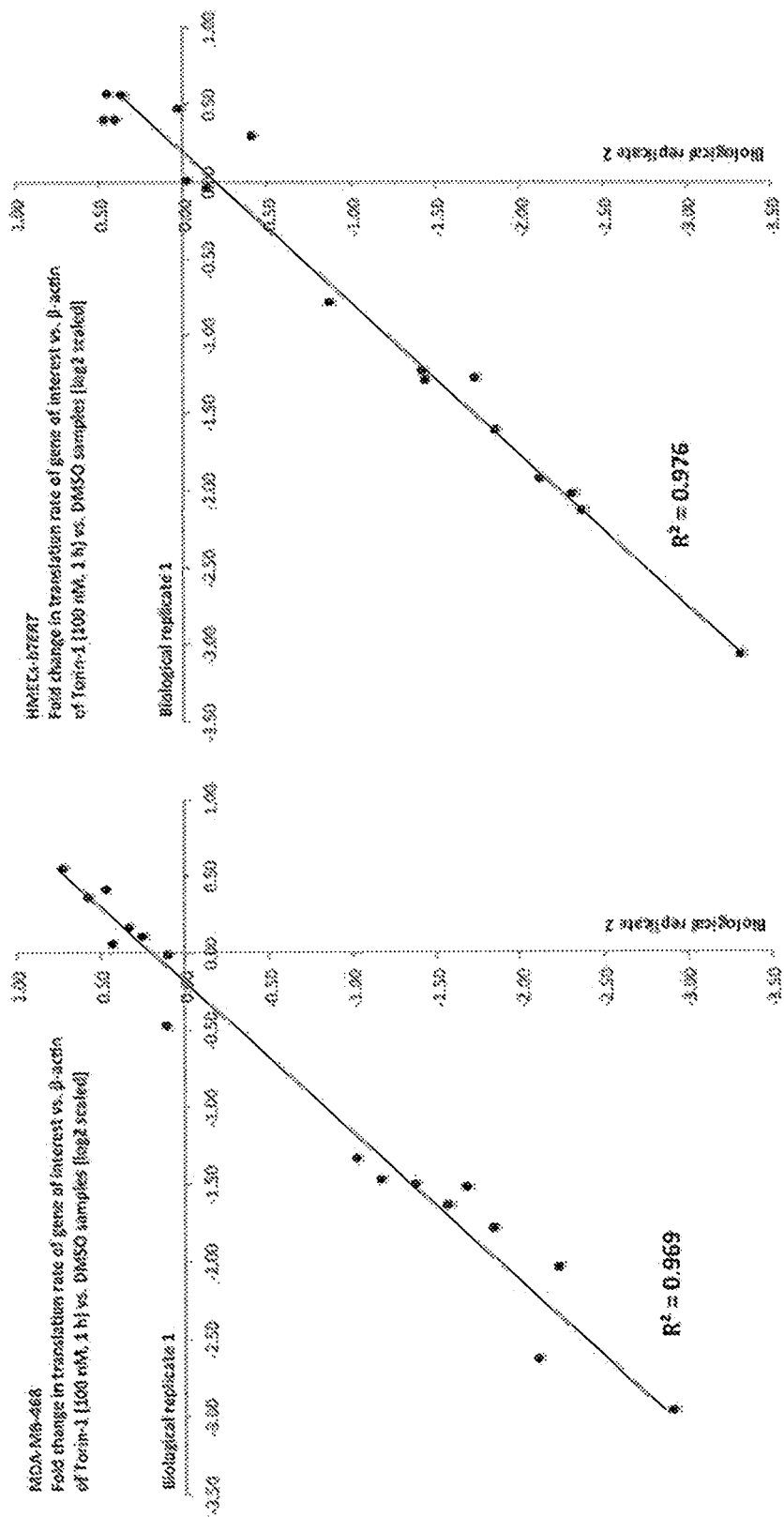
FIG. 5 includes three panels, identified as panels A, B, and C. Panel A shows the reproducibility of mRNA translation determinations made using the methods of the present invention across biological replicates using several different cell lines. Panels B and C show the dissociation curve of the resulting qPCR products of the experiments described in panel A and generally show the formation of a single qPCR product in each sample without substantial formation of additional products, such as primer dimers.
Figure 5:
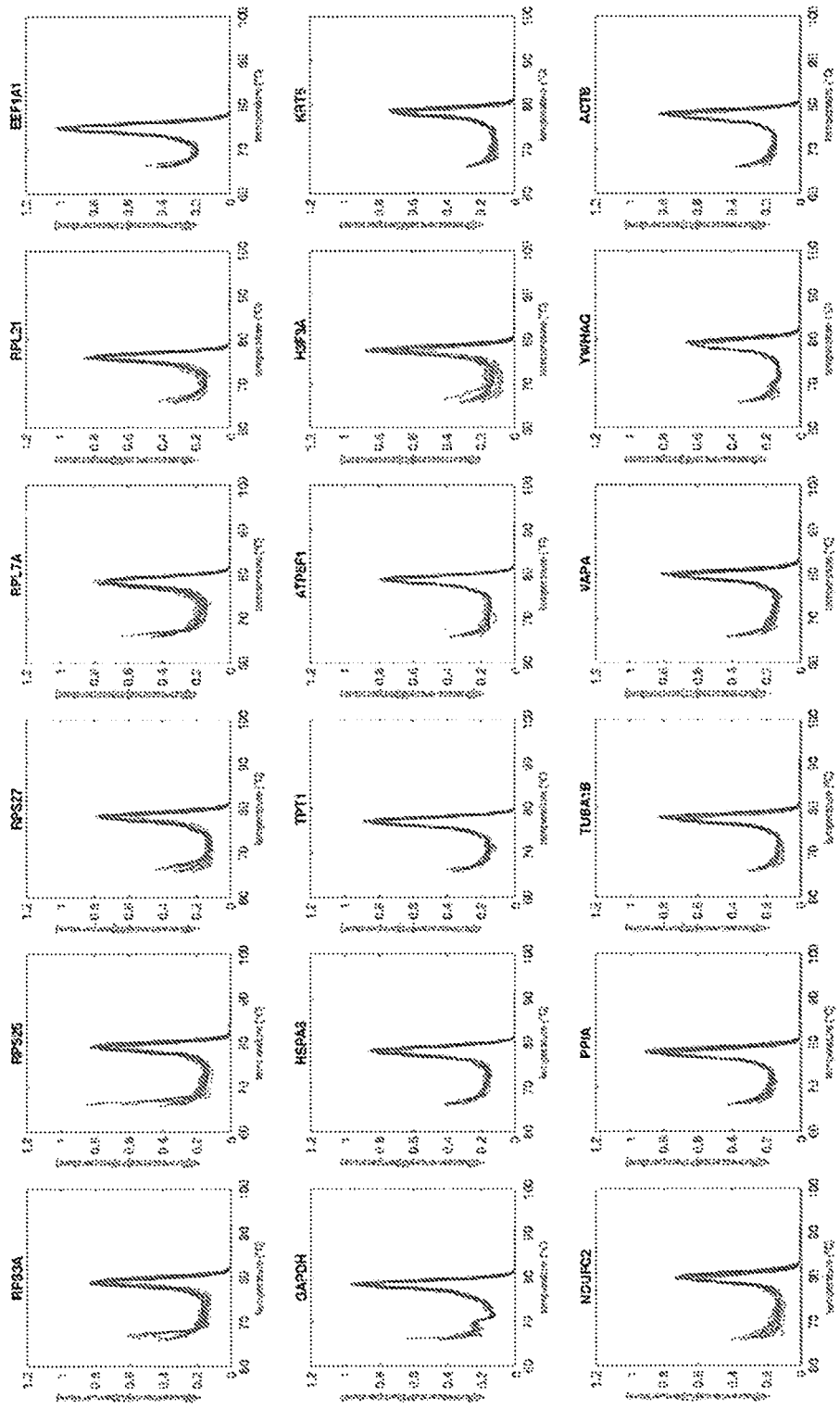
Figure 5:
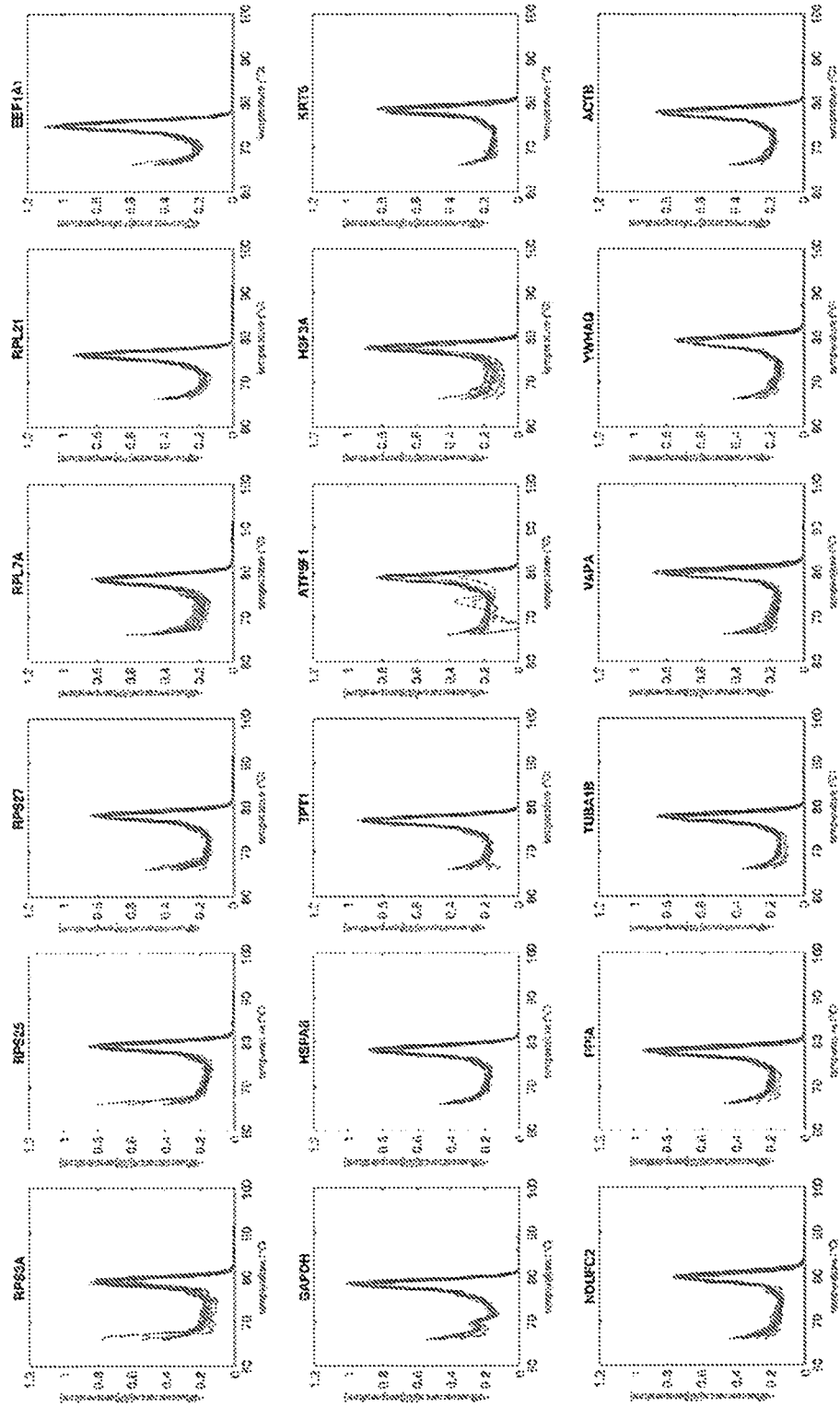

Primer mix A contained a mixture of all of primers A1 to A18 at 1 uM each in water. Primer mix B contained a mixture of two primers, wherein each primer was present at 1 uM in water, one primer was a primer selected from BF1 to BF18 depending upon the target gene of interest, and the second primer was common primer BR. The results of the change in translation rates determined for each of the genes relative to a reference was comparable between the method of the present invention and that of ribosome profiling, which is an established method for determining mRNA translation rates (FIGS. 4 and 6). In addition, FIGS. 5A and 6 demonstrate that the method of the present invention is reproducible across biological replicates of cell lines of interest. FIGS. 5B-5C demonstrate that the method of the present invention generally results in the formation of a single qPCR product in each sample without substantial formation of additional products, such as primer dimers.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of determining the abundance of target RNA bound to ribosomes within a population of RNA-ribosome complexes, comprising:
   a) generating a population of RNA fragments protected from degradation by an agent that degrades nucleic acids that are not protected by a ribosome by
      i) contacting the population of RNA-ribosome complexes with an agent that preferentially pauses the ribosomes at one or more regions of the RNA molecules for a sufficient time to pause the ribosomes at the one or more regions of the RNA molecules, and
      ii) contacting the population of RNA-ribosome complexes with an agent that degrades nucleic acids that are not protected by a ribosome;
   b) converting the undegraded RNA into complementary DNA (cDNA) using reverse transcriptase and at least 2 reverse transcription primers, wherein
      i) the 3' portion of each of the at least 2 reverse transcription primers has a sequence that is substantially complementary to the one or more regions of the RNA molecule or molecules within the population of RNA-ribosome complexes and anneals with the one or more regions of the RNA molecule or molecules at or above the active temperature of the reverse transcriptase,
      ii) the 5' portion of the at least 2 reverse transcription primers has a sequence that is substantially identical to the 3' portion of a reverse amplification primer of step c), and
      iii) each of the at least 2 reverse transcription primers is at least about 6 nucleotides in length;
   c) amplifying the cDNA with polymerase chain reaction (PCR) using a forward and a reverse amplification primer and DNA polymerase to form a detectable number of amplified cDNA of a region of a target RNA, wherein
      i) the 3' portion of the forward amplification primer has a sequence that is substantially complementary to a region that is more 3' of the cDNA as compared with the sequence of the corresponding reverse transcription primer and anneals with the cDNA at or above the active temperature of the DNA polymerase;
      ii) the 3' portion of the reverse amplification primer comprises a sequence that is substantially identical to the 5' portion of the corresponding reverse transcription primer and anneals with the complementary strand of the cDNA or its amplification products formed by extension of the forward amplification primer at or above the active temperature of the DNA polymerase; and
      iii) the PCR product is longer than the length of the reverse transcription primers;
   d) repeating step c) with at least one different forward and/or reverse amplification primer to form a detectable number of amplified cDNA of a region of a different target RNA; and
   e) comparing the amplified cDNA of step c) to the amplified cDNA of step d) to determine the abundance of target RNA bound to ribosomes within the population of RNA-ribosome complexes.

2. The method of claim 1, wherein the RNA of the RNA-ribosome complexes and/or the target RNA is messenger RNA (mRNA), non-coding RNA, long non-coding RNA (lncRNA), untranslated regions of RNA (UTRs), pseudogene RNA, and combinations thereof.

3. The method of claim 1, wherein the population of RNA-ribosome complexes is obtained by lysing cells,
   optionally wherein the cells are lysed with chemical(s) comprising one or more detergents, mechanical disruption, sonication, and/or freezing and thawing, and/or wherein the cells are in a form selected from the group consisting of cultured cells, biopsies, fresh cells, FFPE formalin-fixed paraffin-embedded (FFPE) cells, paraffinized cells, and frozen cells.

4. The method of claim 1, wherein:
   (a) the agent that preferentially pauses the ribosomes at the one or more regions of the RNA molecules is i) cycloheximide and/or derivatives thereof, ii) lactimidomycin, iii) harringtonine and/or derivatives thereof, and combinations thereof;

(b) the one or more regions of the RNA molecules is selected from the group consisting of a translation initiation site and a translation termination site;

(c) the time sufficient to pause the ribosomes at the one or more regions of the RNA molecules is at least 5 seconds;

(d) the agent that degrades nucleic acids that are not protected by a ribosome is selected from the group consisting of DNases and RNases;

(e) the RNA-ribosome complexes are contacted with a DNase prior to, concurrently with, or after contact with an RNase;

(f) the nucleic acids that are not protected by a ribosome are mRNA, non-coding RNA, long non-coding RNA (lncRNA), untranslated regions of RNA (UTRs), pseudogene RNA, and combinations thereof;

(g) the nucleic acids that are not protected by a ribosome are DNA and/or ribosomal RNA;

(h) the RNA-ribosome complexes are contacted with the agent that preferentially pauses the ribosomes at the one or more regions of the RNA molecules before contact with the agent that degrades nucleic acids;

(i) the RNA-ribosome complexes are contacted with the agent that preferentially pauses the ribosomes at the one or more regions of the RNA molecules at the same time as the agent that degrades nucleic acids; and/or (j) the population of RNA fragments protected from degradation is purified prior to converting to cDNA.

5. The method of claim 1, wherein:

(a) the 3' portion of each of the at least 2 reverse transcription primers that is substantially complementary to the one or more regions of the RNA molecule or molecules within the population of RNA-ribosome complexes is within the region that is 30 nucleotides upstream and 30 nucleotides downstream of the one or more regions,
optionally wherein (i) the substantially complementary region is within the region that is 20 nucleotides upstream and 20 nucleotides downstream of the one or more regions, and/or (ii) the substantially complementary region is within the region that is 15 nucleotides upstream and 15 nucleotides downstream of the one or more regions;

(b) the 3' portion of each of the at least 2 reverse transcription primers has a sequence that is substantially complementary to the one or more regions of the RNA molecule or molecules within the population of RNA-ribosome complexes and has a sequence and/or length to anneal with the one or more regions of the RNA molecule or molecules at or above the active temperature of the reverse transcriptase, optionally wherein the 3' portion is the 3' end of the at least 2 reverse transcription primers;

(c) the 5' portion of the at least 2 reverse transcription primers has a sequence that is substantially identical to the 3' portion of a reverse amplification primer of step c), optionally wherein the 5' portion is the 5' end of the at least 2 reverse transcription primers;

(d) the 5' portion of the at least 2 reverse transcription primers has a sequence that is substantially identical to the 3' portion of a reverse amplification primer of step c) has a common sequence among the at least 2 reverse transcription primers for binding the reverse amplification primer of step c);

(e) the RNA binding regions of the at least 2 reverse transcription primers are sufficiently long to bind reverse transcriptase;

(f) the active temperature of the reverse transcriptase is between about 40° C. and 50° C.;

(g) at least 1 of the at least 2 reverse transcription primers is between about 6 and 500 nucleotides in length;

(h) at least 1 of the at least 2 reverse transcription primers comprises a modified base and/or a modified backbone, optionally wherein the modified backbone comprises methylenemorpholine rings and phosphorodiamidate linkages;

(i) at least 1 of the at least 2 reverse transcription primers comprises a detectable label;

(j) at least 2 reverse transcription primers is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 reverse transcription primers; and/or (k) the extension temperature is ramped upward during reverse transcription.

6. The method of claim 1, wherein:

(a) the PCR is real-time PCR, optionally wherein the real-time PCR is quantitative real-time PCR (qPCR);

(b) the binding regions of the forward and reverse amplification primers to the cDNA template and amplification products are sufficiently long to bind the DNA polymerase;

(c) the forward amplification primer specifically binds cDNA converted from the target RNA and the reverse amplification primer specifically binds the complementary strand of the cDNA converted from the target RNA;

(d) the active temperature of the DNA polymerase is at least about 50° C.;

(e) at least 1 of the forward or reverse amplification primers comprises a modified base and/or a modified backbone, optionally wherein the modified backbone comprises methylenemorpholine rings and phosphorodiamidate linkages;

(f) at least 1 of the forward or reverse amplification primers comprises a detectable label;

(g) at least 1 of the forward or reverse amplification primers comprises a detectable label and the detectable label(s) is one or more fluorophores, optionally wherein the fluorophore(s) is a dye whose fluorescence intensity and/or spectrum changes upon binding to double-stranded DNA or a fluorescently labeled nucleic acid probe;

(h) the annealing and extension cycle temperature is ramped upward within each cycle during PCR amplification;

(i) amplified cDNA is not sequenced;

(j) the cDNA and/or amplified cDNA is not used to produce a cDNA library;

(k) the PCR product is about 20 to about 500 base pairs in length; and/or (l) the PCR product is about 50 to about 150 base pairs in length.

7. The method of claim 1, wherein the RNA-ribosome complexes, undegraded RNA, cDNA, and/or amplified cDNA is not size-selected on a gradient or gel.

8. A method of determining the abundance of target RNA bound to ribosomes within a population of RNA-ribosome complexes, comprising:

a) generating a population of RNA fragments protected from degradation by an agent that degrades nucleic acids that are not protected by a ribosome by i) contacting the population of RNA-ribosome complexes with an agent that preferentially pauses the ribosomes at one or more regions of the RNA molecules for a sufficient time to pause the ribosomes at the one or more regions of the RNA molecules, and ii) contacting the population of RNA-ribosome complexes with an agent that degrades nucleic acids that are not protected by a ribosome;

b) converting the undegraded RNA into complementary DNA (cDNA) using reverse transcriptase and at least 1 reverse transcription primer, wherein i) the 3' portion of each of the at least 1 reverse transcription primer has a sequence that is substantially complementary to the one or more regions of the RNA molecule or molecules within the population of RNA-ribosome complexes and anneals with the one or more regions of the RNA molecule or molecules at or above the active temperature of the reverse transcriptase, ii) the 5' portion of the at least 1 reverse transcription primer has a sequence that is substantially identical to the 3' portion of a reverse amplification primer of step c), and iii) the at least 1 reverse transcription primer is at least about 6 nucleotides in length;

c) amplifying the cDNA with polymerase chain reaction (PCR) using a forward and a reverse amplification primer to form a detectable number of amplified cDNA of a region of a target RNA, wherein i) the 3' portion of the forward amplification primer has a sequence that is substantially complementary to a region that is more 3' of the cDNA as compared with the sequence of the reverse transcription primer and anneals with the cDNA at or above the active temperature of the DNA polymerase;

ii) the 3' portion of the reverse amplification primer comprises a sequence that is substantially identical to the 5' portion of the reverse transcription primer and anneals with the complementary strand of the cDNA or its amplification products formed by extension of the forward amplification primer at or above the active temperature of the DNA polymerase; and iii) the PCR product is longer than the length of the reverse transcription primer;

d) repeating steps b) and c) with at least one different reverse transcription primer and at least 1 different forward and/or reverse amplification primer to form a detectable number of amplified cDNA of a region of a different target RNA; and e) comparing the amplified cDNA of step c) to the amplified cDNA of step d) to determine the abundance of target RNA bound to ribosomes within the population of RNA-ribosome complexes.

9. The method of claim 8, wherein steps b) and c) are performed in the same vessel, and/or wherein the reverse transcriptase of step b) is heat inactivated before or during step c) and the DNA polymerase in step c) is heat activated.

10. The method of claim 8, wherein the RNA of the RNA-ribosome complexes and/or the target RNA is messenger RNA (mRNA), non-coding RNA, long non-coding RNA (lncRNA), untranslated regions of RNA (UTRs), pseudogene RNA, and combinations thereof.

11. The method of claim 8, wherein the population of RNA-ribosome complexes is obtained by lysing cells, optionally wherein (i) the cells are lysed with chemical(s) comprising one or more detergents, mechanical disruption, sonication, and/or freezing and thawing, and/or (ii) the cells are in a form selected from the group consisting of cultured cells, biopsies, fresh cells, FFPE formalin-fixed paraffin-embedded (FFPE) cells, paraffinized cells, and frozen cells.

12. The method of claim 8, wherein:

(a) the agent that preferentially pauses the ribosomes at the one or more regions of the RNA molecules is i) cycloheximide and/or derivatives thereof, ii) lactimidomycin, iii) harringtonine and/or derivatives thereof, and combinations thereof;

(b) the one or more regions of the RNA molecules is selected from the group consisting of a translation initiation site and a translation termination site;

(c) the time sufficient to pause the ribosomes at the one or more regions of the RNA molecules is at least 5 seconds;

(d) the agent that degrades nucleic acids that are not protected by a ribosome is selected from the group consisting of DNases and RNases, optionally wherein the RNA-ribosome complexes are contacted with a DNase prior to, concurrently with, or after contact with an RNase;

(e) the nucleic acids that are not protected by a ribosome are mRNA, non-coding RNA, long non-coding RNA (lncRNA), untranslated regions of RNA (UTRs), pseudogene RNA, and combinations thereof;

(f) the nucleic acids that are not protected by a ribosome are DNA and/or ribosomal RNA;

(g) the RNA-ribosome complexes are contacted with the agent that preferentially pauses the ribosomes at the one or more regions of the RNA molecules before contact with the agent that degrades nucleic acids, or the RNA-ribosome complexes are contacted with the agent that preferentially pauses the ribosomes at the one or more regions of the RNA molecules at the same time as the agent that degrades nucleic acids; and/or (h) the population of RNA fragments protected from degradation is purified prior to converting to cDNA.

13. The method of claim 8, wherein:

(a) the 3' portion of each of the at least 1 reverse transcription primers that is substantially complementary to the one or more regions of the RNA molecule or molecules within the population of RNA-ribosome complexes is within the region that is 30 nucleotides upstream and 30 nucleotides downstream of the one or more regions, optionally wherein the substantially complementary region is within the region that is 20 nucleotides upstream and 20 nucleotides downstream of the one or more regions, or wherein the substantially complementary region is within the region that is 15 nucleotides upstream and 15 nucleotides downstream of the one or more regions;

(b) the 3' portion of each of the at least 1 reverse transcription primers has a sequence that is substantially complementary to the one or more regions of the RNA molecule or molecules within the population of RNA-ribosome complexes and has a sequence and/or length to anneal with the one or more regions of the RNA molecule or molecules at or above the active temperature of the reverse transcriptase is the 3' end of the at least 1 reverse transcription primers;

(c) the 5' portion of the at least 1 reverse transcription primers has a sequence that is substantially identical to the 3' portion of a reverse amplification primer of step c) is the 5' end of the at least 1 reverse transcription primers;

(d) the 5' portion of the at least 1 reverse transcription primers has a sequence that is substantially identical to the 3' portion of a reverse amplification primer of step c) has a common sequence among the at least 1 reverse transcription primers for binding the reverse amplification primer of step c;
(e) the RNA binding regions of the at least 1 reverse transcription primers are sufficiently long to bind reverse transcriptase;
(f) the at least 1 reverse transcription primers specifically bind cDNA converted from the target RNA;
(g) the active temperature of the reverse transcriptase is between about 40° C. and 50° C.;
(h) at least 1 of the at least 1 reverse transcription primers is between about 6 and 500 nucleotides in length;
(i) at least 1 of the at least 1 reverse transcription primers comprises a modified base and/or a modified backbone, optionally wherein the modified backbone comprises methylenemorpholine rings and phosphorodiamidate linkages;
(j) at least 1 of the at least 1 reverse transcription primers comprises a detectable label;
(k) at least 1 reverse transcription primers is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 reverse transcription primers; and/or
(l) the extension temperature is ramped upward during reverse transcription.

14. The method of claim 8, wherein:
(a) the PCR is real-time PCR, optionally wherein the real-time PCR is quantitative real-time PCR (qPCR);
(b) the binding regions of the forward and reverse amplification primers to the cDNA template and amplification products are sufficiently long to bind the DNA polymerase;
(c) the forward amplification primer specifically binds cDNA converted from the target RNA and the reverse amplification primer specifically binds the complementary strand of the cDNA converted from the target RNA;
(d) the active temperature of the DNA polymerase is at least about 50° C.;
(e) at least 1 of the forward or reverse amplification primers comprises a modified base and/or a modified backbone, optionally wherein the modified backbone comprises methylenemorpholine rings and phosophorodiamidate linkages;
(f) at least 1 of the forward or reverse amplification primers comprises a detectable label;
(g) at least 1 of the forward or reverse amplification primers comprises a detectable label and the detectable label(s) is one or more fluorophores, optionally wherein the fluorophore(s) is a dye whose fluorescence intensity and/or spectrum changes upon binding to double-stranded DNA or a fluorescently labeled nucleic acid probe;
(h) the annealing and extension cycle temperature is ramped upward within each cycle during PCR amplification;
(i) the amplified cDNA is not sequenced;
(j) the cDNA and/or amplified cDNA is not used to produce a cDNA library;
(k) the PCR product is about 20 to about 500 base pairs in length; and/or
(l) the PCR product is about 50 to about 150 base pairs in length.

15. The method of claim 8, wherein the RNA-ribosome complexes, undegraded RNA, cDNA, and/or amplified cDNA is not size-selected on a gradient or gel.

16. The method of claim 1, wherein the abundance of target RNA bound to ribosomes within a population of RNA-ribosome complexes indicates the translation rate of the target RNA.

17. The method of claim 8, wherein the abundance of target RNA bound to ribosomes within a population of RNA-ribosome complexes indicates the translation rate of the target RNA.

* * * * *